US012607179B2

(12) United States Patent
Arrizza et al.

(10) Patent No.: US 12,607,179 B2
(45) Date of Patent: Apr. 21, 2026

(54) PERISTALTIC PUMPING DEVICE AND MEDICAL APPARATUS, IN PARTICULAR FOR DIALYSIS, INCORPORATING IT

(71) Applicant: COREQUEST SAGL, Lugano (CH)

(72) Inventors: Fabio Arrizza, Fossacesia (IT); Silvio Borrelli, Cercola (IT); Arduino Arduini, Arogno (CH)

(73) Assignee: COREQUEST SAGL, Lugano (CH)

( * ) Notice: Subject to any disclaimer, the term of this patent is extended or adjusted under 35 U.S.C. 154(b) by 360 days.

(21) Appl. No.: 18/567,900

(22) PCT Filed: Jun. 8, 2022

(86) PCT No.: PCT/EP2022/065602
§ 371 (c)(1),
(2) Date: Dec. 7, 2023

(87) PCT Pub. No.: WO2022/258716
PCT Pub. Date: Dec. 15, 2022

(65) Prior Publication Data
US 2024/0261481 A1 Aug. 8, 2024

(30) Foreign Application Priority Data

Jun. 11, 2021 (IT) ........................ 102021000015332

(51) Int. Cl.
*F04B 43/12* (2006.01)
*A61M 1/28* (2006.01)
(Continued)

(52) U.S. Cl.
CPC ........... *F04B 43/0009* (2013.01); *A61M 1/28* (2013.01); *A61M 5/14228* (2013.01);
(Continued)

(58) Field of Classification Search
CPC ................ A61M 1/28; A61M 5/14228; A61M 2205/0216; A61M 2205/106;
(Continued)

(56) References Cited

U.S. PATENT DOCUMENTS 4,482,347 A 11/1984 Borsanyi
6,270,326 B1 8/2001 Kuriyama
(Continued)

FOREIGN PATENT DOCUMENTS

EP 0200448 A2 11/1986
JP 2007120355 A 5/2007
(Continued)

OTHER PUBLICATIONS

R. Popovich, et al. "Continuous Ambulatory Peritoneal Dialysis" Annals of Internal Med. vol. 88; Apr. 4, 1978. pp. 303-310.
(Continued)

*Primary Examiner* — John Kim
(74) *Attorney, Agent, or Firm* — Volpe Koenig

(57) ABSTRACT

A peristaltic pumping device of linear type, includes a section of deformable tube crossed by a fluid whereon at least a peristaltic compression is implemented; and an actuator, including a rotating element provided with one or more helical ribs arranged projecting from its surface to interfere, along the rotation of the rotating element, with said deformable tube and, so as to determine thereon at least a localized, movable and continuous squeezing, moving along a predetermined direction, which implements peristaltic compression, the helical ribs are arranged along a helical axis with respect thereto they are fixed, the position thereof being tied with respect to the rotating element, wherein at least a portion of helical rib, which interferes with said deformable tube, is rotatable around the respective helical axis, thereby minimizing the friction thereof on the surface
(Continued)

of the deformable tube, thereby allowing to reduce effectively the stress on the deformable tube.

20 Claims, 13 Drawing Sheets

(51) Int. Cl.
    *A61M 5/142*     (2006.01)
    *F04B 43/00*     (2006.01)

(52) U.S. Cl.
    CPC .......... *F04B 43/12* (2013.01); *F04B 43/1223* (2013.01); *A61M 2205/0216* (2013.01); *A61M 2205/106* (2013.01); *A61M 2205/121* (2013.01); *A61M 2205/331* (2013.01); *A61M 2205/3327* (2013.01); *A61M 2205/3331* (2013.01); *A61M 2205/3368* (2013.01); *A61M 2205/6045* (2013.01)

(58) Field of Classification Search
    CPC ...... A61M 2205/121; A61M 2205/331; A61M 2205/3327; A61M 2205/3331; A61M 2205/3368; A61M 2205/6045; F04B 43/0009; F04B 43/12; F04B 43/1223
    See application file for complete search history.

(56) References Cited

U.S. PATENT DOCUMENTS

| | | | |
|---|---|---|---|
| 2011/0144567 | A1 | 6/2011 | Sorensen |
| 2011/0242234 | A1 | 10/2011 | Jones |
| 2014/0241923 | A1 | 8/2014 | Nzike |

FOREIGN PATENT DOCUMENTS

| | | | |
|---|---|---|---|
| SU | 402683 | A1 | 10/1973 |
| WO | 9953201 | | 10/1999 |
| WO | 2019211782 | A1 | 11/2019 |
| WO | 2021068546 | A1 | 4/2021 |

OTHER PUBLICATIONS

S.T. Boen, et al. "Periodic Peritoneal Dialysis in the Management of Chronic Uremia." Dept. of Medicine and Surgery, University of Washington. pp. 256-262, ASAIO Journal 8(1), Apr. 1962.

PERISTALTIC PUMPING DEVICE AND MEDICAL APPARATUS, IN PARTICULAR FOR DIALYSIS, INCORPORATING IT

BACKGROUND OF THE INVENTION

Technical Field

The present invention relates to a peristaltic pumping device, of linear type, wherein a fluid is pushed along a substantially linear tube the section thereof can be elastically deformed by an actuator element which presses and deforms such a tube.

Moreover, the invention relates to a medical apparatus incorporating said pumping device, in particular an apparatus for dialysis, with particular reference to a cycler for the automated peritoneal dialysis (CAPD or CCPD), wherein a dialysis solution is slowly removed and supplied from and towards a patient.

Peritoneal dialysis (PD) represents a concrete therapeutic opportunity available to the nephrological class and integrates with haemodialysis and kidney transplant for the treatment of chronic terminal uraemia.

The so-called Continuous Ambulatory Peritoneal Dialysis (CAPD), proposed for the first time in 1976 [Continuous ambulatory peritoneal dialysis—R P Popovich, J W Moncrief, K D Nolph, A J Ghods, Z J Twardowski, W K Pyle—Ann. Intern. Med. 1978 April; 88(4): 449-56, PMID: 637423], is a continuous manual method of peritoneal dialysis (PD) consisting in filling up the abdomen (intraperitoneal space), through a suitable indwelling catheter, with a dialysis sterile solution, for example with a high concentration of glucose (high osmotic concentration), and discharging it after few hours.

CAPD exploits the concentration difference of the solutes between the body water and the dialysis solution as well as osmotic concentration of such liquid. The drainage of the fluid loaded in abdomen allows the removal of uremic toxins from organism, apart from water and exceeding sodium, which in the meantime have transferred to the dialysis solution. At the end of such a drainage, new sterile fluid is immediately inserted in abdomen.

This drainage/loading procedure is called "exchange", on the whole it lasts approximately 30 minutes and it is usually performed four times in 24 hours.

The permanence of the dialysis liquid in abdomen (dwell-time) is classically 5 hours for 3 times (day stasis) and 9 hours (night stasis) but it can be modified according to the patient's needs.

CAPD can include 3 exchanges in 24 hours, more frequently 4, up to 5, with volumes loaded for each exchange which more frequently are more than 2 litres, and can be customized according to the patient's body mass.

The Automated Peritoneal Dialysis (APD) is a peritoneal dialysis automated method which uses a medical apparatus called cycler [Boen S T, et al. Periodic peritoneal dialysis in the management of chronic uraemia. Trans Amer Soc Artif Intern Organs 1962; 8:25-62].

The patient, once the treatment features have been set in the cycler, is subjected to automatic exchanges (loading and discharge of the solution) which usually take place by night and, on the whole, they last 8-9 hours, and the overall used dialysis solution volumes vary from about 6 to 25 litres.

The exchanges are of variable number, more frequently from 3 to 8, and they can take place with the complete drainage of the abdomen or with the mode called tidal, by means thereof the drainage, and the subsequent loading, are set on the cycler as percentage (from 50% to 75%) of the initial loading volume.

The mechanisms for the peritoneal transport of the uremic toxins and water are similar to those of CAPD even because the dialysis solutions have the same composition.

If APD, at the end of its cycle, performs one last dialysis solution loading, thus by making the peritoneal dialysis active in all 24 hours (day full abdomen), it is called Continuous Cycling Peritoneal Dialysis (CCPD) or Continuous Tidal Peritoneal Dialysis (CTPD).

Hereinafter the medical apparatus of the present invention, by way of example, can be a cycler for CAPD, APD, CCPD, CTPD, or another apparatus which has to guarantee an inflow and an outflow, with controlled and constant flows, of a fluid, in a pumping of peristaltic type comprising an actuator element.

Under actuator element, herein and hereinafter, a screw-conveyor or screw rotating element is meant, which has one or more projecting helical ribs, arranged so as to press and squeeze the deformable tube of the peristaltic pump, by causing on it or more compression points moving on the tube length at constant speed in a determined direction, which is determined by the rotation direction of the actuator element.

Therefore, under peristaltic pumping device of linear type a peristaltic pump is meant which exploits a longitudinal, in case but not necessarily rectilinear, extension, instead of a circular curve thereof.

Then, the linear peristaltic devices distinguish from the roller or wheel peristaltic devices since the pressure on the deformable tube is exerted on a tube extension in linear position, by projections which substantially slide continuously on the length of the deformable tube, which, in turn, can be contemporarily stressed by more than one projection simultaneously.

The fluid which is contained in the deformable tube, which generally could have a liquid or pasty consistence, is then pushed forward by the above-mentioned compression points.

However, it is meant that the pumping device could be applied to any apparatus which can use it, both in the health sector and in other not medical sectors, to cause the flowing of a liquid or a low-pressure paste.

In the medical context, and in particular within dialysis, the peristaltic pumps are generally used for the extracorporeal circulation of the blood flow.

In the peritoneal dialysis, a physiological solution of dialysis type is inserted in the peritoneal cavity of a patient's abdomen, so that it absorbs, through the peritoneal membranes of the abdomen peritoneal cavity, which are highly vascularized, the toxins existing in the blood. Subsequently, such exhausted solution is extracted from the abdomen and the cycle in case is repeated.

The insertion of the dialysis solution and its extraction from the patient's abdomen represent the critical steps of the peritoneal dialysis, since they need a strict and precise control over timing, quantities and treatment modes.

Moreover, all these procedures have to be performed with the maximum asepticity of the portions coming in contact with the patient and with the solution which is inserted in his/her body, to avoid the onset of infections.

It is then to be considered that the apparatuses which perform this task can be used in outpatient environment, by even low-skilled medical staff, or can be usually entrusted to the patients, which use them often autonomously in domestic and not hospital environment, even while sleeping.

Therefore, they have to be particularly reliable, robust and simple to be used. In fact, any malfunction of the apparatus, and any difficulty in the dialysis procedure deriving from the wrong use of the cycler, which cannot be solved immediately, could have serious consequences on the patient's health and life.

Moreover, it is requested that the apparatus for the peritoneal dialysis, and then in particular its pumping device, are compact and provide a use as intuitive as possible.

At last, considering that this type of devices must not have economic obstacles for its spreading, it has to be simple to be implemented. In particular, the portions which have to be disposable must be the less expensive ones and with reduced dimensions. It is further requested that their use is simplified as much as possible.

Description of the Prior Art

The above-described problems unite at least partially the peritoneal dialysis with other medical procedures wherein the above-described pumping device can be used.

Several types of medical apparatuses which use at least a pumping device to inject, extract or circulate a fluid through a suitable catheter are known, but their use often has excessive complications, even deriving from the complexity of their structure.

U.S. Pat. No. 6,270,326 B1 describes a device for transfusions comprising, among the various shown solutions, even a peristaltic pump of the screw conveyor type wherein a compression is exerted along the whole length of a section of deformable tube, but without a system causing simultaneously the return of the tube part section in a normal configuration, i.e. with the maximum passage section.

International patent application No. WO 99/53201 A1 describes a peristaltic pump wherein a section of deformable tube is compressed alternatively according to directions perpendicular to each other, to obtain a peristaltic effect and, separately, to deform the tube in an opposite way to that of the peristaltic effect, to ease the return thereof to a normal section.

US patent application No. 2011/242,234 A1 describes a peristaltic device wherein a section of deformable tube is compressed, on its own length, by a series of pistons acting in sequence to exert a peristaltic compression on the tube.

European patent application No. EP 0,200,448 A2 describes a linear peristaltic pump wherein the actuator element is a rotating cylindrical element having a helical projection on its surface.

Even Japanese patent application N. JP 2007/120,355 A describes a linear peristaltic pump, wherein the helical projection is obtained by wrapping an additional tube around a rotating cylindrical element.

Patent application in USA No. 2011/0,144,567 A1 describes a suction pump acting on a disposable cartridge containing a tube section with deformable section, and a screw rotating element acting on such tube.

International patent application No. WO 2021/068546 A1 describes a linear peristaltic pump wherein one single rotating actuator element, with a helical projection, acts on a plurality of tubes inserted between said rotating actuator element and a containment cylindrical armour.

International patent application No. WO 2019/211782 A1, at last, describes an apparatus for the peritoneal dialysis comprising a device of peristaltic type with a screw conveyor element which, by rotating, determines a movable compression along a deformable tube, the not compressed shape thereof is restored by a sequence of deformable rods acting laterally of the tube itself.

A drawback particularly felt in the above-described linear peristaltic pumping devices lies in the continuous stress thereto the deformable tube is subjected for prolonged periods of time.

By using the dialysis field by way of example, despite the section of deformable tube can be replaced, the single dialysis session provides the slow outflow, in a direction and in the opposite direction, of even considerable amounts of solution for the dialysis, and this requires that the flow through the tube, and then its mechanical performances in terms of deformability, do not change during the whole session.

For this reason, it is fundamental that the tube could be stressed under compression, however while keeping unaltered its mechanical functionality during session, with wide safety margins.

Although some of the above-described peristaltic pumps try to mitigate the problem by easing, as soon as the compression ceases, the return of the tube section to its original shape, the rotating actuators of the screw or screw conveyor type substantially cause a sliding between the respective projecting elements pressing on the tube and the surface of the tube itself, which sliding causes a sliding friction and then a wear and an overheating of the tube, therefrom a degradation of its performances on a prolonged time interval derives.

Such time interval, the duration thereof is not certainly compatible with a continuous operation of the pumping device in fields other than the medical one and peritoneal dialysis, is not however even compatible with the duration of one single treatment of peritoneal dialysis, at the end thereof the deformable tube can and must be replaced, since in these fields the precision in the performances of the pump and of its tube have to be constant and exactly predictable.

For this reason, cyclers are known using different injection and suction systems, such as syringes and the like, which offer constant performances, repeatable over time, but which increase complexity and use difficulty of the medical apparatus.

SUMMARY OF THE INVENTION

The technical problem underlying the present invention is to provide a pumping device, in particular but not exclusively for medical apparatuses, which allows to obviate the drawback mentioned with reference to the known art.

Such problem is solved by a pumping device as specified above, and as defined in the enclosed claim 1, which then allows to reduce effectively the stress on the deformable tube and to simplify the use of the machine system and of the disposable kit by the patient.

Additional aspects of the invention are defined in the enclosed depending claims. The invention further relates to a medical pumping apparatus comprising at least a peristaltic pump as detailed hereinafter.

In the pumping device of the present invention, a section of deformable tube is provided, arranged in a linear, i.e. substantially rectilinear, layout placed inside a linear seat having a bottom whereupon a lower surface of the tube section is rested, whereas on the upper surface it is faced to an actuator of the pumping device comprising a rotating element around an axis in agreement to the linear development of the above-mentioned section of deformable tube.

The section of deformable tube is crossed by a fluid, which can consist in a liquid, creamy fluid or a paste, which is pumped by the pumping device: on the tube section a peristaltic compression is implemented.

The peristaltic compression is determined by a substantially cylindrical screw or screw conveyor rotating element, or of the type provided with one or more helical ribs arranged projecting from the surface of the rotating element so as to interfere, along the rotation of the rotating element, with the deformable tube, so as to determine, along said section of deformable tube, at least a localized movable and continuous squeezing, moving along a predetermined direction: such movable squeezing constitutes said peristaltic compression, and the direction according to which the continuous squeezing moves determines the flowing direction of the fluid flow.

The helical ribs are arranged along a helical axis with respect thereto they are fixed, their position being tied with respect to the rotating element.

In the device according to the invention, at least the portion of helical rib which interferes with said deformable tube in turn is revolving around the respective helical axis, and then it is capable of rotating around such axis, however remaining in its position with respect to the surface of the rotating element, thereby minimizing the sliding of the helical rib, and then the sliding friction correlated thereto, on the surface of the deformable tube.

It is meant that, in order to minimize said sliding, considering the substantial concordance between the rotation axis of the rotating element and the direction in which said helical axis develops, the rotation direction of the rotating element and the rotation direction of the helical nerve are opposite to each other.

In other words, if an observer turns towards the rotating element and a portion of the helical nerve from a position in which the rotation axis of the rotating element and a line tangent to the corresponding portion of helical axis is nearly parallel to such axis, or converges as far as almost intersecting such axis, they see that the rotation direction of the rotating element and the rotation direction of the helical rib are opposite: if one rotates clockwise the other one will rotate counter-clockwise or vice versa.

This rotation direction will result both when the portion rotation is a consequence of the fact of being revolving and of its interaction with the deformable tube (passive rotation), and when such portion is made to rotate by mechanisms assigned to this purpose (active rotation).

In a preferred embodiment of the invention, said helical ribs consist of a flexible linear element, structurally independent from the rotating cylindrical element, spirally wound in a helical pattern around it and kept in a fixed position on its surface.

In this way, during the rotation of the rotating cylindrical element, this linear element acts as projecting rib, by determining a squeezing on the deformable tube which moves longitudinally along a direction which determines the direction of the fluid inside the deformable tube.

In the device according to this embodiment of the invention the whole linear element, extending in its winding by following a helical axis, is capable of rotating around such axis, by keeping its helical arrangement on the rotating cylindrical element, so as to minimize the friction thereof, and then the sliding friction correlated thereto, on the surface of the deformable tube.

In other words, the linear element wound in helical way rotates in its seat on the cylindrical surface of the rotating cylindrical element, and then rolls on the surface of the deformable tube by compressing it, with a rotation direction so as to minimize and in case to annul the friction thereof on the tube surface.

In this way, a lower stress of the tube and then a reduction of its wear over time is obtained, by giving to the linear peristaltic pumping device, which keeps unaltered its advantage in terms of limiting the pressure pulses in the fluid, even the typical advantages of the roller peristaltic pump, i.e. the rolling of the element pressing on the tube surface.

The rolling of the linear element wound in helical way can be induced in a passive way by the same friction between itself and the surface of the deformable tube, and on this matter the linear element could be assembled on suitable self-lubricating bearings or supports in its helical path on the rotating cylindrical element.

Advantageously, on the rotating cylindrical element a helical recess is obtained acting as seat of the linear element wound in helical way, which can be single and include at least a winding along the rotating cylindrical element, in such a way that the deformable tube is always compressed in at least one point, so that the fluid transfer inside the tube is continuous, and preferably in at least two spaced points.

According to a preferred version of the present invention, the linear element wound in a helical pattern is rotated actively, by driving into rotation its ends arranged at the ends of the rotating cylindrical element.

Advantageously, the rotation of the linear element wound in helical way is synchronized with the rotation of the rotating cylindrical element, by means of respective sets of gears which couple the two distinct rotations, so that a variation in the rotation speed of the rotating cylindrical element of the pumping device determines a corresponding variation in the rotation of the linear element wound in a helical way around its helical axis.

According to a preferred version of the present invention, the above-mentioned synchronization is so that a rotation of the rotating cylindrical element corresponds to a proportional rotation of the linear element wound in a helical way around its helical axis, according to a predetermined ratio which determines, on the deformable tube, a pure rolling, and a friction substantially of rolling type.

According to a preferred version of the present invention, the linear element wound in helical way is a chain.

According to a preferred version of the present invention, the chain is formed by a sequence of chain elements connected therebetween; they have a curved, preferably rounded, surface and they are connected therebetween through a joint which implements a coupling substantially of cardan type.

According to an alternative embodiment, the helical rib can consist of a sequence of independent elements aligned therebetween along a helical axis, and each independent element is capable of rotating around such axis, by keeping its helical arrangement on the rotating cylindrical element, thereby minimizing the friction thereof, and then the sliding friction correlated thereto, on the surface of the deformable tube.

Such rotation can be induced passively by the interference between the independent element and the deformable tube, or the rotation of all independent elements can be controlled actively, for example by a dedicated actuator arranged inside the rotating element of the pumping device.

In the linear peristaltic pumping device, simultaneously to said continuous squeezing determined by the chain element, on the lateral surfaces of the tube, i.e. those separating said lower resting and upper squeezing surfaces, means act to compress laterally the section of deformable tube elastically.

Such compression is continuous, and it is exerted on the whole length of the tube section whereon the peristaltic compression is compressed, but it is so as not to prevent the squeezing of the tube section caused by the movable peristaltic compression: this guarantees an immediate and continuous return of the section of the tube part to its starting configuration, i.e. that with maximum extension.

To this purpose, according to a preferred version of the present invention, the deformable tube is contained in a linear seat formed by a longitudinal recess wherein the tube is inserted; this linear seat is formed in a hollow supporting element with deformable walls, closed hermetically and wholly filled up with a substantially incompressible fluid, which then occupies the whole available inner space.

In this way, the squeezing of the deformable tube in its seat in turn determines a deformation of the supporting element at the squeezing: it causes a shifting of the incompressible fluid inside the supporting element which, at the not compressed tube portions, causes a lateral constriction of the tube caused by the pressure inside the supporting element. Such constriction is so as to bring the section of the deformable tube, as soon as the squeezing of the tube has ended, back to its natural shape.

An additional advantage of the pumping device according to the present invention then lies in its operation reliability and simplicity, coupled with a considerable structural robustness. Moreover, it allows using tubes made of not perfectly elastic behaviour material with respect to the currently used silicone tubes, but more resistant and reliable.

BRIEF DESCRIPTION OF DRAWINGS

The present invention will be described hereinafter according to a preferred embodiment thereof, within a medical apparatus for the peritoneal dialysis, provided by way of example and not with limitative purposes with reference to the enclosed drawings, wherein:

FIG. 4A shows a cross section view of the apparatus of FIG. 1, in a closed operation configuration thereof, taken along the plane B-B of FIG. 4;

FIG. 26A shows a view in longitudinal section of the chain section of FIG. 24, taken along the plane A-A of FIG. 26;

DESCRIPTION OF AN EMBODIMENT EXAMPLE OF THE INVENTION

Figure 1:
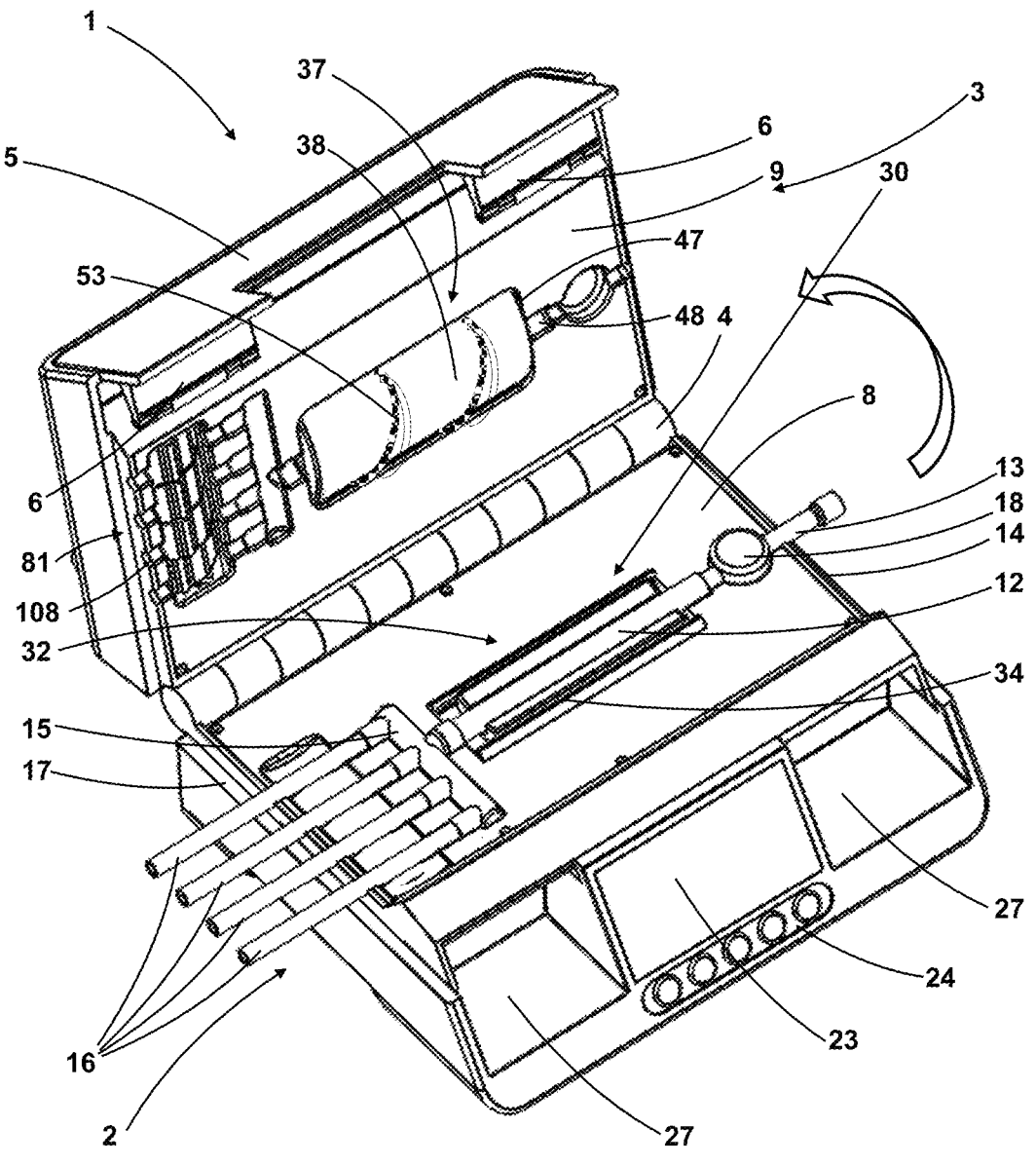
FIG. 1 shows an axonometric view of a medical apparatus, in particular for the automated peritoneal dialysis (APD), of the cycler type, in an open configuration thereof, incorporating a pumping device according to the invention and comprising a section of kit for peritoneal dialysis.
Figures 2, 3:
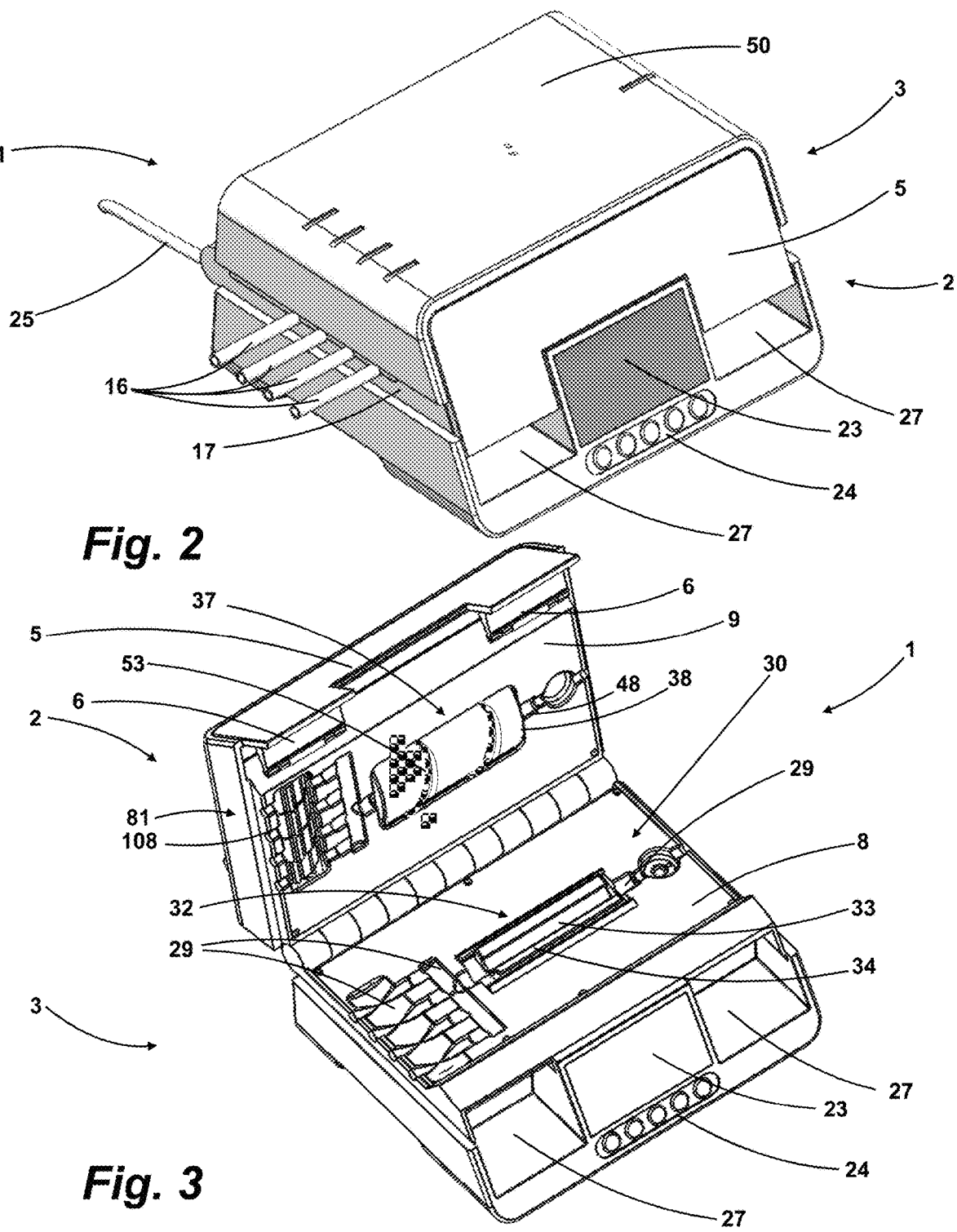
FIG. 2 shows an axonometric view of the apparatus of FIG. 1, in a closed operation configuration thereof.
FIG. 3 shows an axonometric view of the apparatus of FIG. 1, in an open configuration thereof, however without the section of kit for peritoneal dialysis.

With reference to FIGS. 1 to 4, a medical apparatus, of the type usable within the automated peritoneal dialysis as cycler, is designated as a whole with 1. It comprises a base portion 2 and an upper, or cover, portion designated with 3, which are revolvingly constrained therebetween by means of a hinge 4 extending on a whole side of the portions 2, 3, thanks thereat the upper portion 3 can rotate with respect to the base portion 2 from a closed configuration (FIGS. 2 and 4A), wherein the two portions 2, 3 form one single box-like casing which corresponds to the operating configuration of the cycler, to a wholly open position (FIGS. 1, 3 and 4C), wherein the inside of the apparatus 1 is accessible and wherein the cycler is disabled to operation.

The upper portion 3 comprises frontally, on the opposite side with respect to that of the hinge 4, a snap closure with a revolving handle 5, hinged to the edge of the upper portion 3 and projecting therefrom.

Figure 4:
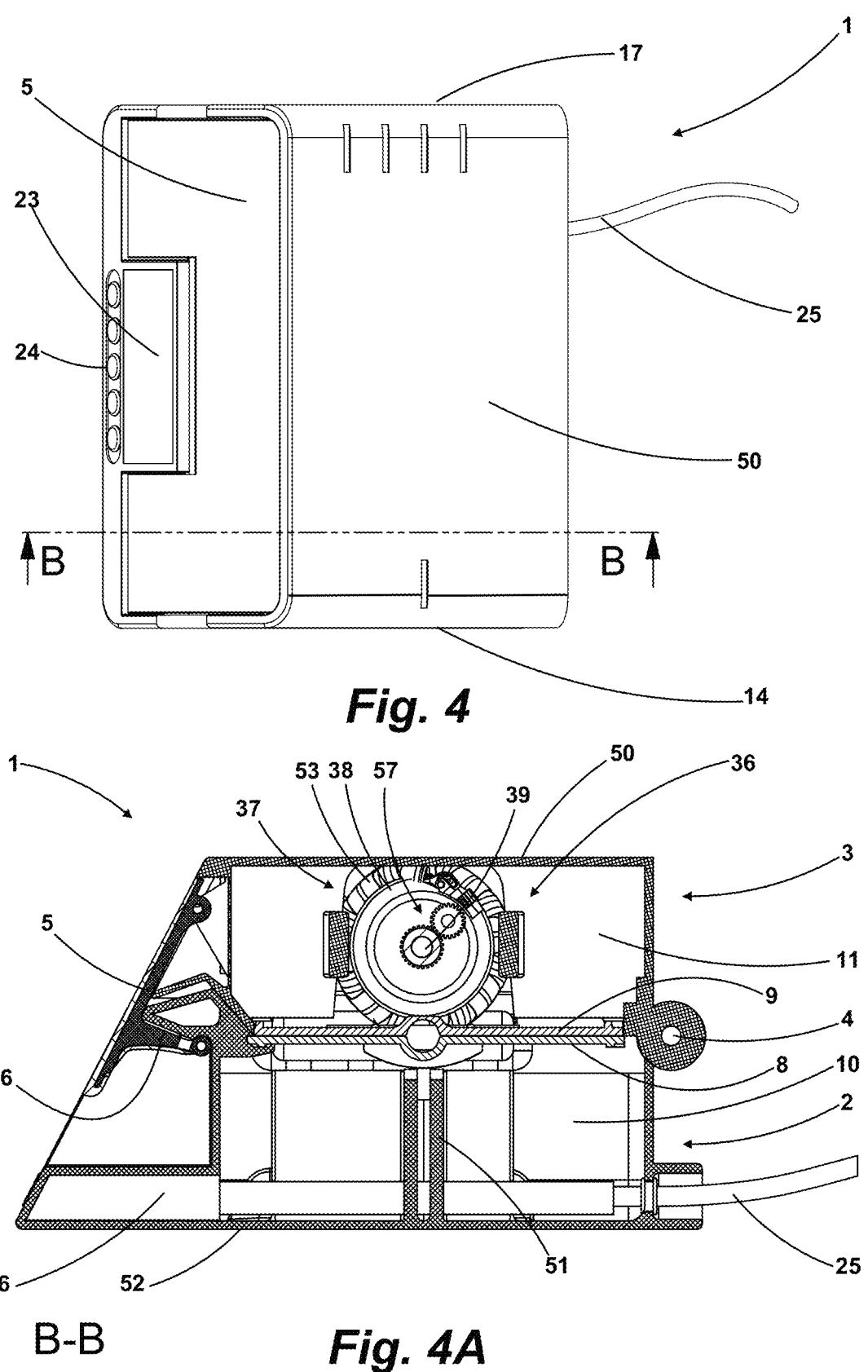
FIG. 4 shows a top plan view of the apparatus of FIG. 1, in a closed operation configuration thereof.
Figures 4B, 4C:
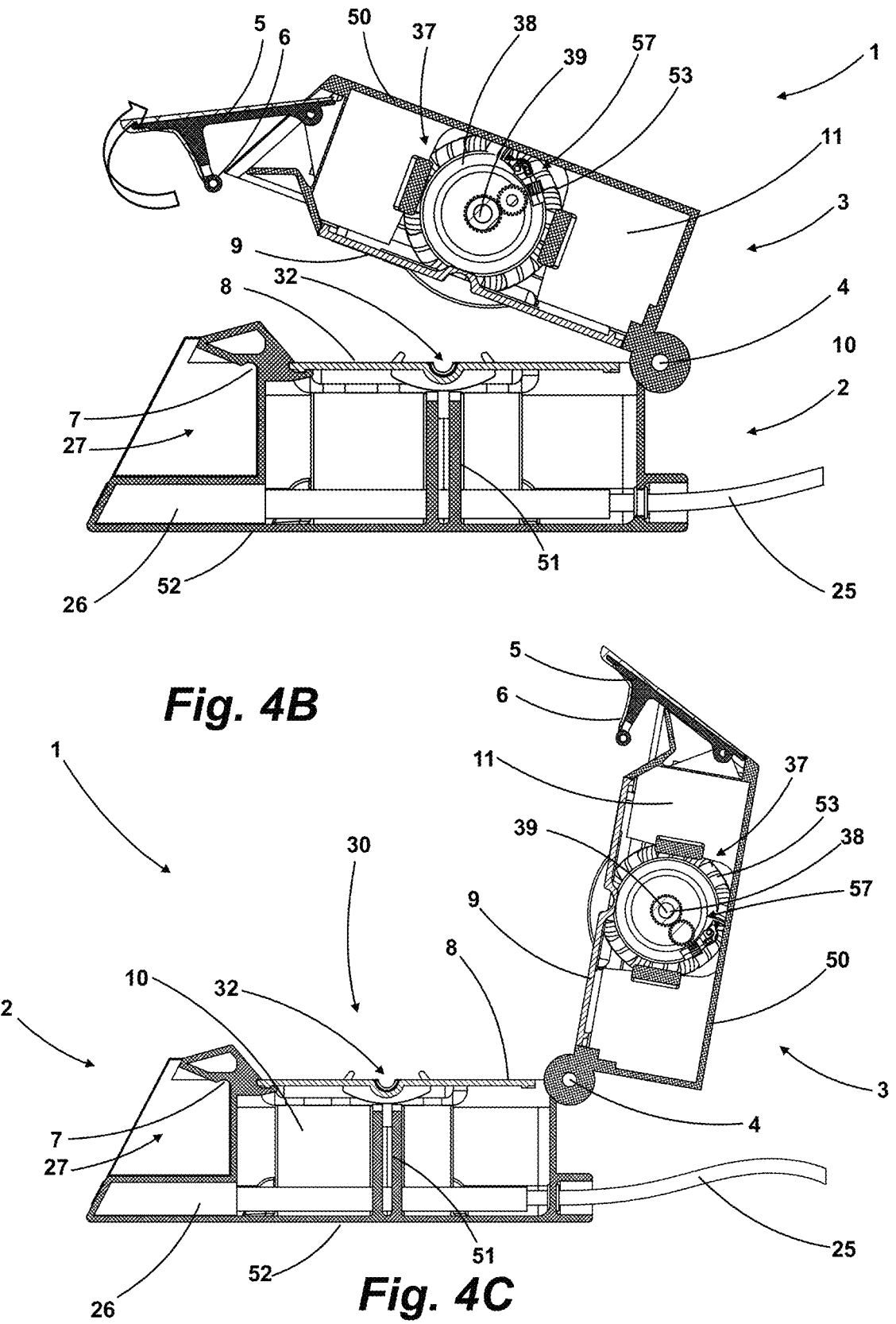
FIG. 4B shows a cross section view of the apparatus of FIG. 1, in a partially open configuration thereof.
FIG. 4C shows a cross section view of the apparatus of FIG. 1, in a wholly open configuration thereof.

The revolving handle 5, which is revolvingly hinged to the casing of the upper portion 3, extends on the whole front side of the apparatus 1 and it can be grasped thanks to two grasping openings 27 which open on said front side: by inserting the fingers in one or both such openings it is possible to move the handle 5, forwards, by making it to rotate upwards (FIG. 4B).

The revolving handle 5, at its ends, comprises a respective closing tooth 6 adapted to be snap engaged and disengaged in and from a corresponding closing recess 7 arranged on the corresponding edge of the base portion 2.

The complete insertion of the closing teeth 6 in their recesses 7 presses a (not shown) switch and/or activates a sensor, for example a magnetic sensor, which enables the operation of the apparatus 1 only when it is wholly closed.

The base portion 2 and the upper portion 3 comprise respective first and second interior wall, designated with 8 and 9, which, in the closed configuration, adhere therebetween (FIG. 4A). Such interior walls 8 and 9 define, in the respective base and upper portion 2, 3, a respective base and upper compartment, designated with 10 and 11.

In open configuration, the upper portion 3 and the base portion 2 form an internal angle of approximately 120° therebetween, which allows an easy access to the interior walls 8, 9 of both of them, and of all portions which are herein localized and which will be described hereinafter.

Figures 5, 6, 7:
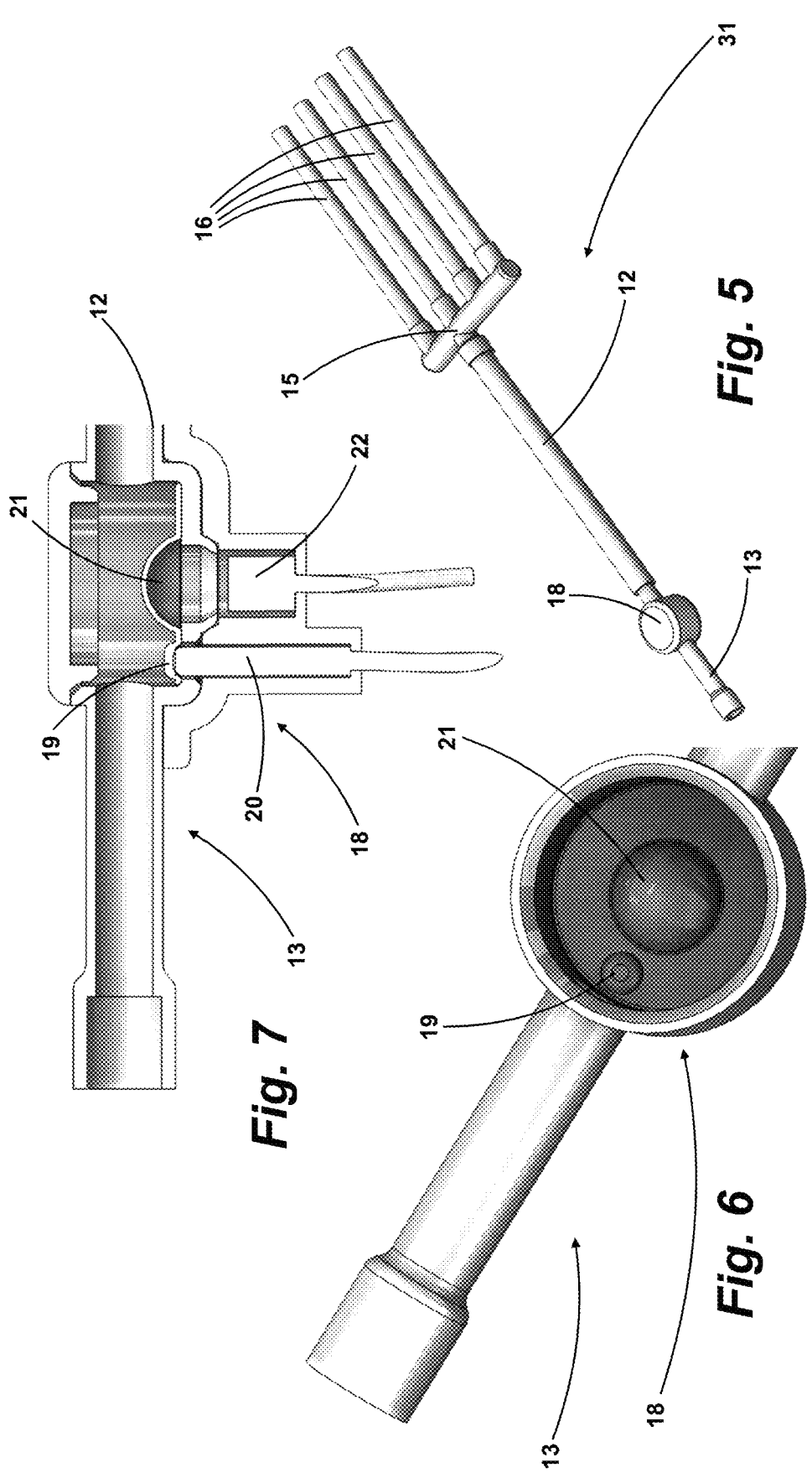
FIG. 5 shows an axonometric view of the section of kit for peritoneal dialysis inserted in the apparatus of FIG. 1.
FIG. 6 shows an enlarged axonometric view of a detail of the section of kit for peritoneal dialysis of FIG. 5.
FIG. 7 shows a view in longitudinal section of the detail of the section of kit for peritoneal dialysis of FIG. 6.

On the first interior wall 8 an operating seat 30 is formed (FIG. 3) which is arranged to receive a section of kit for peritoneal dialysis, designated as a whole with 31 (FIG. 5).

Generally, a kit for peritoneal dialysis comprises a plurality of loading bags which contain a dialysing physiological solution for the peritoneal dialysis which has to be inserted in a patient's abdomen so that it fills up its peritoneal cavity. The physiological solution contains substances facilitating the molecular exchange between the peritoneal membrane and the solution itself, in case in different amounts.

Moreover, the kit comprises at least a discharge bag useful, at the end of a treatment period, to collect the exhausted dialysis solution which absorbed an amount of impurities from the patient's blood. At the end of the process, the "dirty" solution then has to be sucked from the peritoneal cavity so that it is accumulated in a discharge bag.

The insertion and extraction take place through a peritoneal catheter which is inserted surgically in the patient's abdomen and which has a distal end with a connector, which is useful to connect the peritoneal catheter with a duct implemented by a tube made of elastically flexible material, in particular a rubbery material.

Such tube constitutes the deformable tube of the peristaltic pumping device which will be described hereinafter, and it is integrating portion thereof. The tubes used in the peristaltic pumps are usually made of materials with high elasticity and typically with silicone base, whereas the tubes used in the kits for peritoneal dialysis are made of less elastic materials, such as for example PVC, but however chemically suitable to the contact with the dialysis solution.

The section of kit for peritoneal dialysis 30 of FIGS. 1 and 7 is the section of kit comprised between a connector which connects it to the patient's abdominal catheter, and to additional connectors which connect it to bags for loading and discharging pure or exhausted dialysis solution. It comprises said deformable tube 12, extending from a proximal end thereof 13, adapted to be connected to the peritoneal catheter, arranged on a proximal side 14 of the apparatus 1, to a distal end 15 consisting of a branching comprising, in this example, four connecting lines 16 which, in turn, will be connected to the above-mentioned loading and discharge bags. The distal end 15 is arranged on a distal side 17 of the apparatus 1, whereas said proximal end 13 outgoes (FIG. 1) from said proximal side 14 to connect to a patient's abdominal catheter through a not represented connector.

Said connecting lines 16 consist of flexible and deformable tubes, which can be clamped to lock the fluid outflow inside.

The above-mentioned proximal end 13 of the deformable tube 12 comprises a seat for sensors 18, formed by a cylindrical casing, the axis thereof is herein perpendicular to the extension of the deformable tube 12 flowing inside thereof and branches therefrom so as to constitute one single hydraulic section crossed by the fluid passing through the deformable tube 12, with an internal space wide enough to house the requested sensors.

Internally, on a base surface thereof faced towards the base portion 2, the seat for sensors 18 comprises a socket 19 connected to a first capillary duct 20, and a deformable dome 21 which defines its own internal space connected to a second capillary duct 22.

The sensible needle of a sensor for measuring the temperature of the liquid passing in the seat 18 can be inserted in the first capillary duct 20: the seat would be obstructed by the inserted needle and the electric signal representing the temperature is sent to a control unit.

The second capillary duct 22 is connected to a corresponding, not shown, pressure transducer, received in the base portion 2 of the apparatus 1, for generating a corresponding pressure electric signal which is sent to a control unit.

It is to be meant that even several sensors, such as for example optical sensors, can be present, acting through a transparent window of the seat 18, which are capable of verifying the presence of air in the circuit of fluids, performing an examination of the fluid turbidity, or identifying particular chemical compounds by lightening the passing fluid with a light, for example generated by a LED or by a laser, through said transparent window, and by examining the spectrum of the reflected light.

The position of the seat for sensors 18 shown in figures is purely exemplifying, in fact it can be arranged near the distal end 15, for example it could be connected to a derivation of the branching shown in figure. Alternatively, two seats could be present, at the respective ends of the deformable tube 12.

In the base compartment 10 of the base portion 2, said control unit is received, designated with 26, it comprises an interface for processing the signals, at least a microprocessor and at least a memory, for managing the dialysis process.

All above-mentioned transducers and sensors are received in the apparatus 1, specifically in the base portion 2, and they are connected to the control unit 26.

Tale control unit 26 is connected to a display 23, in case of touch type, and a keyboard 24, with output and input functions. Moreover, an acoustic warning device and a possible voice synthesizer can be provided, connected to a voice register, for alarms and warnings. The keyboard can further include keys with an internal lightning showing to the user the ongoing process step.

A power cable 25 for the power supply of the control unit and of the peristaltic pumping device which will be described hereinafter is also connected to the base portion 2. The power supply preferably will be at low voltage.

Additionally, the apparatus can include a preferably rechargeable back-up battery, to obviate possible voltage drops during the dialysis process which, for obvious reasons, cannot be interrupted.

The operating seat 30 (FIG. 3) of the section of kit for peritoneal dialysis 31 comprises a base recess 29, obtained in the first interior wall 8, on the face directed upwards, which has a lowered shape, complementary to that of the kit for peritoneal dialysis 31, in particular to receive the ends 13, 15 of the kit 31, the seat for sensors 18 in a predetermined position, and the connecting lines 16 at the distal side 17 of the base portion 2.

The complementarity between the shapes of the kit for peritoneal dialysis 31 and of its seat consisting of the base recess 29 guarantees that only the kit of provided type can be inserted in the apparatus, thus preventing the use of not appropriate kits, or an improper use of the pumping device.

Centrally, the operating seat 30 in turn comprises a linear seat 32 for the deformable tube 12, extending longitudinally to the centre of the first interior wall 8. The linear seat 32 comprises a longitudinal recess 33 wherein said section of deformable tube 12 of the kit 31 is inserted, and then it has a bottom whereupon a lower surface of the tube section is rested, whereas on the upper surface it is directed upwards.

In the present pumping device then means is provided to compress laterally the section of deformable tube 12 acting on the whole peristaltic compression length thereof and acting continuously and simultaneously to the peristaltic compression, so as not to influence the fluid flow which has to remain constant and determinable with precision.

The pressure therewith said lateral compression is exerted, however, is so as to allow the peristaltic squeezing of the section of deformable tube 12, which is movable and which then is not hindered in its motion, to restore the normal passage part of the section of deformable tube 12 when said squeezing is not exerted.

In this regard, the linear seat 32 further comprises a hollow supporting element 34 with deformable walls, wherein said longitudinal recess 33 is formed, wherein the hollow supporting element 34 is wholly filled up with a substantially incompressible fluid, which then occupies the whole available inner space thereof 35. Hereinafter the operation of the supporting element 34 within the herein described pumping device will be shown in details.

Figures 16, 17:
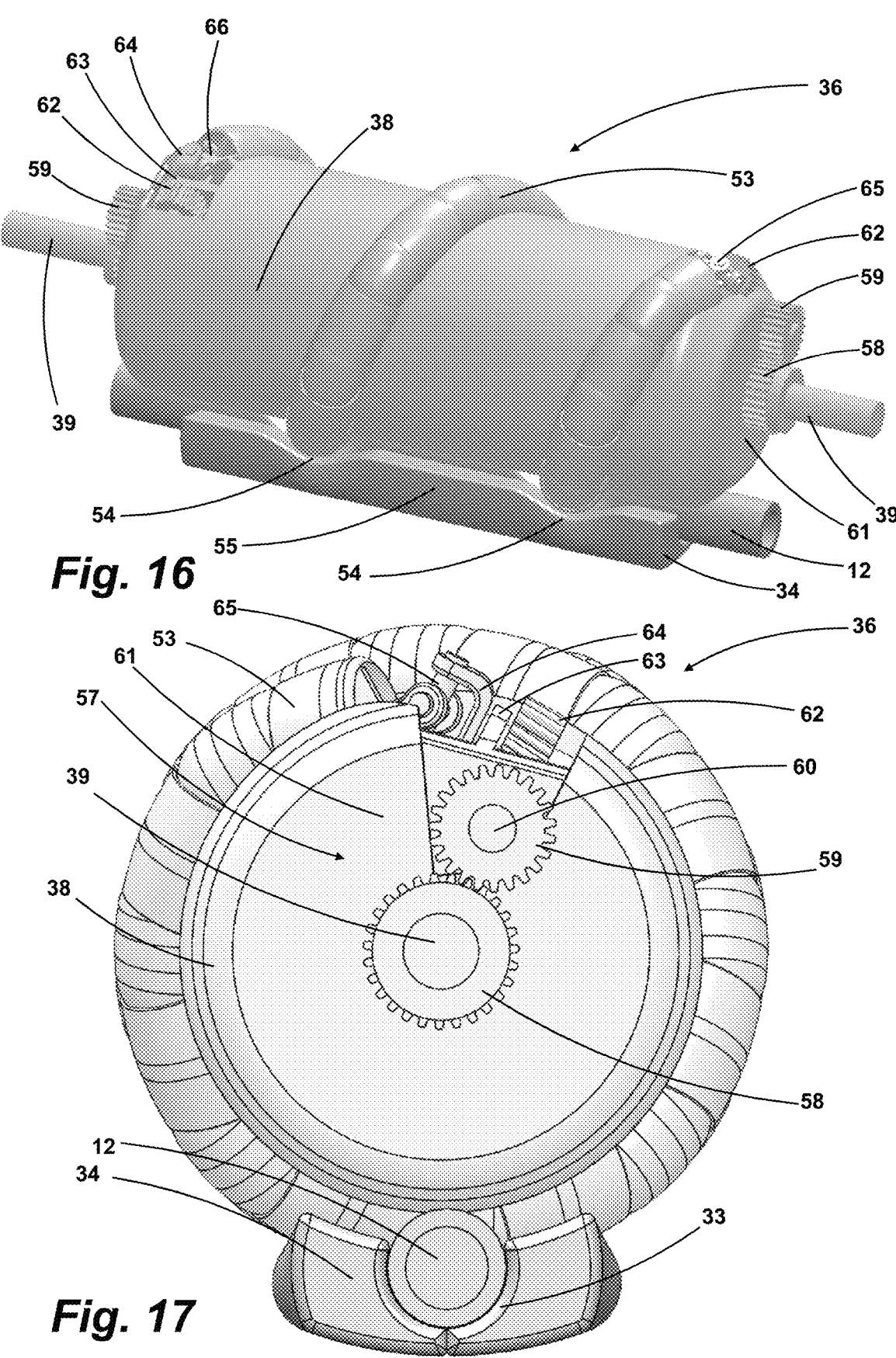
FIG. 16 shows a partial axonometric view of the pumping device, incorporated in the medical apparatus of FIG. 1, in an operating configuration.
FIG. 17 shows a partial side view of the pumping device of FIG. 16.
Figures 18, 19, 20, 21:
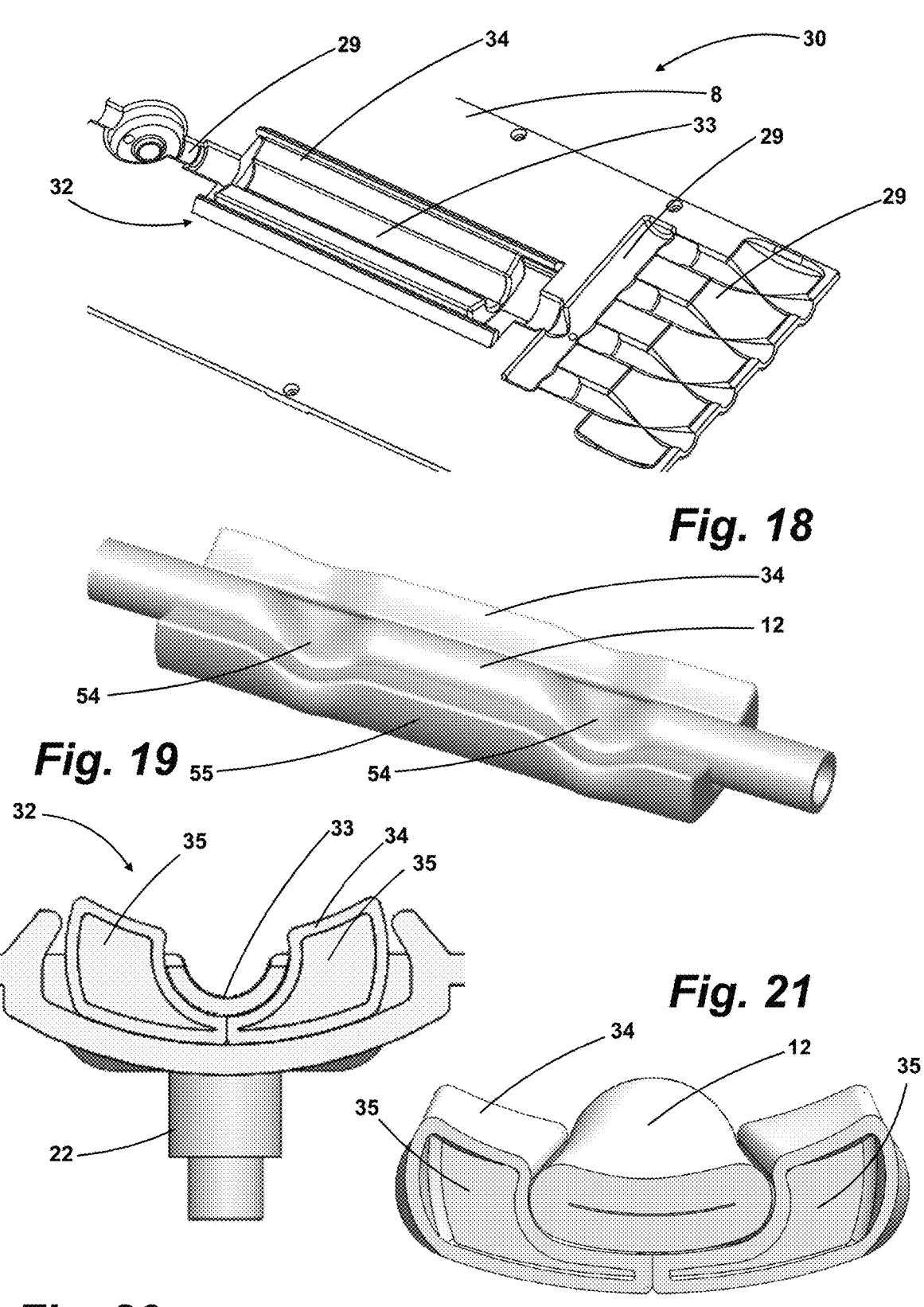
FIG. 18 shows an axonometric view of another portion of the pumping device incorporated in the medical apparatus of FIG. 1, partially visible too.
FIG. 19 shows an axonometric view illustrating the interaction between the portions and a catheter part belonging to the section of kit for peritoneal dialysis inserted in the apparatus of FIG. 1.
FIGS. 20 and 21 show cross section views of the interaction of FIG. 19, in a not compressed configuration, wherein the catheter is only partially visible, and in a compressed configuration, respectively.

The herein described medical apparatus 1 incorporates a pumping device represented as a whole in FIG. 16, and designated with 36; it consists of several components which are housed both in the base portion and in the upper portion 3.

The pumping device 36 of peristaltic type comprises a deformable tube to be compressed in peristaltic way which in the present case, in particular consists of the section of deformable tube 12 of the kit for peritoneal dialysis 31 which, as specified previously, is crossed by a fluid whereon at least a peristaltic compression is implemented. In the present example such fluid is a liquid, i.e. the pure dialysis solution, to be inserted in the patient's abdomen, or exhausted dialysis solution, to be extracted and stored in suitable bags.

Moreover, as it will be more evident hereinafter, the pumping device 36 even comprises said linear seat 32, which receives the deformable tube for the peristaltic compression, i.e. said section of deformable tube 12.

The pumping device 36 comprises an actuator, designated as a whole with 37, in turn comprising a rotating element 38 with cylindrical shape, which has a driven shaft 39 which is sustained by a proximal shaft support 40 and by a distal shaft support 41 at the ends of the rotating element 38. The driven shaft 39 comprises a first actuation wheel 42, preferably of toothed type, which is driven into rotation by a first belt 43, preferably toothed too to implement a direct transmission, in turn connected to a first driving wheel 44, fastened to a first driving shaft 45 of a first motor 46, in particular an electric motor powered at low voltage.

The first motor 46 is powered with variable voltage, to vary both the rotation speed of the rotating element 38 and the rotation direction thereof, so that the flowing direction of the fluid in the deformable tube could vary. The power supply of the first motor 46 is controlled through said control unit, based upon the input commands and pre-set operation programmes.

The rotation axis of the rotating element 38, identified by the driven shaft 39, is substantially parallel to the second interior wall 9 and to the longitudinal axis of the longitudinal recess 33 formed in the supporting element 34, and then it is even parallel to the longitudinal axis of the deformable tube 12 when it is inside thereof.

Figures 8, 9:
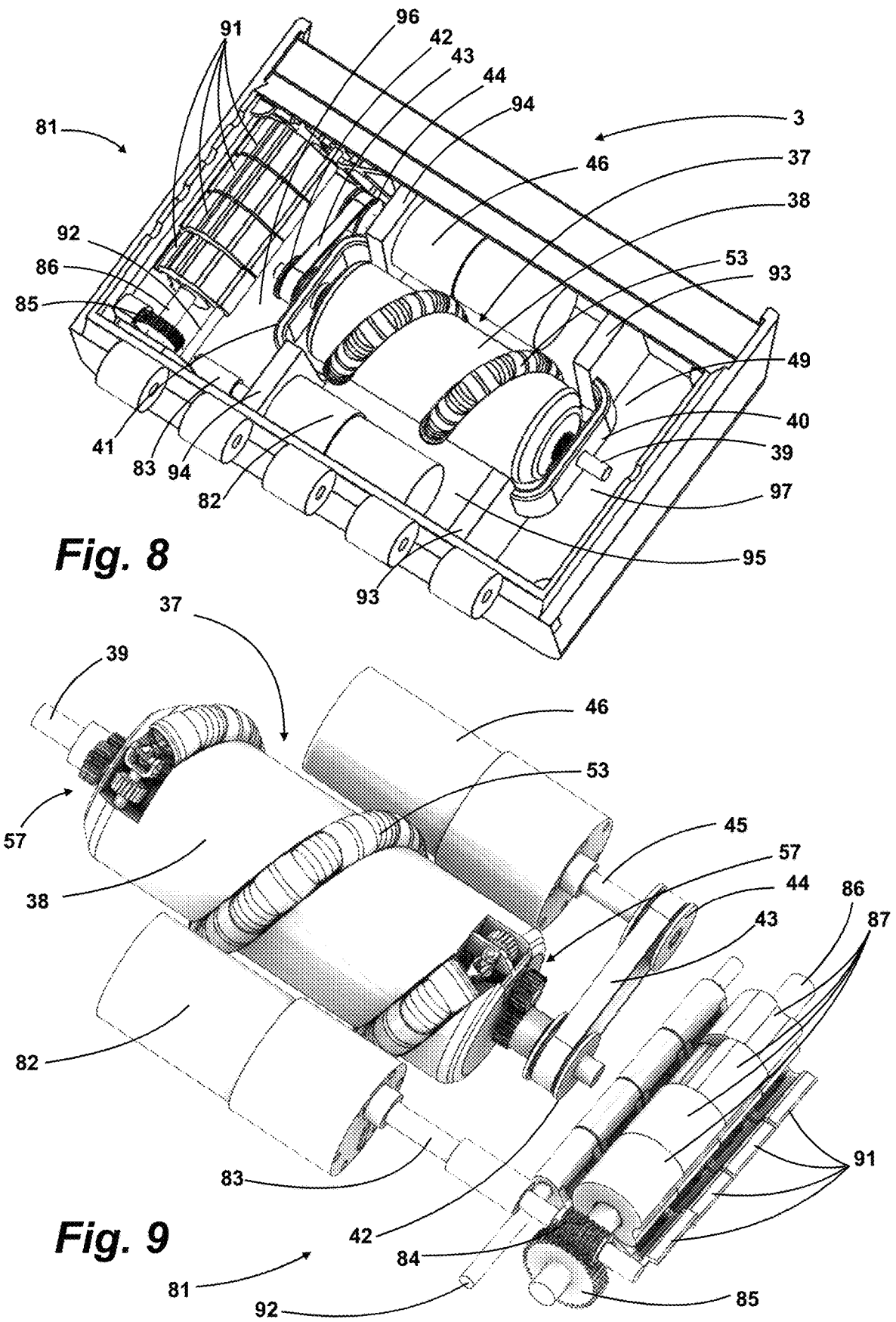
FIG. 8 shows an axonometric and partial section view of a cover portion of the apparatus of FIG. 1, illustrating a portion of the pumping device incorporated therein and a portion of the apparatus itself.
FIG. 9 shows an axonometric view of some components of the cover portion of FIG. 8, shown isolated.

The above-described whole actuator 37 and the first motor 46 are received in the upper compartment 11 of the upper portion 3, and are hidden by the second interior wall 9, whereon said proximal and distal shaft supports 40, 41, projecting from an interior face 49 of the top wall 50 (FIG. 8) of the upper portion 3, substantially connect thereto. The second interior wall 9 comprises a first window 47 therefrom a portion of the rotating element 38 projects, facing towards the base portion 2 when the apparatus 1 is in the closed (FIG. 4A) and half-open (FIG. 4B) configuration.

From the internal face 49 of the top wall 50 even two pairs of respectively proximal 93 and distal 94 dividing septa project vertically, the septa of each pair, together with the proximal and distal shaft supports 40, 41 therewith they form substantially two dividing planes, divide the internal space of the upper compartment 11 into three areas: a central area 95 receiving the actuator 37, a distal area 96 substantially corresponding to said connecting lines 16 and to their branching from the section of deformable tube 12, and a proximal area 97.

It is to be noted that the section of the first driving shaft 45 comprised between the first motor 46 and the first driving wheel 44 crosses the distal dividing septum 93 thereby it is sustained.

In this way, in the above-mentioned closed configuration with the kit 31 inserted in its destination seat 30, the rotating element 38 adheres (FIG. 4A) to the deformable tube 12, the upper portion thereof is facing towards said actuator 37 of the pumping device 36.

The second interior wall 9 further comprises an upper recess 48 to receive the section of kit 31 for the peritoneal dialysis, complementary to the base recess 29.

It is also to be noted that the base portion 2 comprises inside thereof a longitudinal double-wall septum 51 projecting vertically from the bottom wall 52, which sustains the interior wall at the base recess 29, and in particular the section of deformable tube 12 where, as it will result clear hereinafter, the pressure exerted by the actuator 37 concentrates.

The actuator 37 is provided with one or more helical ribs, in the present example in particular one single helical rib designated with 53, wrapping on the rotating element 38 extending from one end to the other one with two windings.

Said one or more helical ribs 53 are spirally wound on the surface of the rotating element, thus defining a helical axis determined by such winding, with respect thereto the position thereof is tied as it is then with respect to the surface of the rotating element 38.

In particular, in this embodiment example, on the rotating element 38 a helical recess 56 is obtained for each helical rib, then one in the present example, acting as its seat by constraining the position thereof.

The helical rib 53 is arranged projecting from the cylindrical surface of the rotating element 38, and then, when the apparatus 1 is in closed configuration with the section of kit 31 in its position, and when the peristaltic pumping device 36 is under operating conditions, the helical rib 53 interferes and squeezes, along the rotation of the rotating element, said deformable tube 12 (FIGS. 16 and 17).

Then, it is to be meant that, in this way, on the section of deformable tube 12 at least a localized squeezing 54 is determined, each one corresponding to a coil of the cylindrical rib 53. Such squeezing, due to the effect of the rotation of the rotating element 38, is movable and continuous, and it moves in a predetermined direction, in this way by implementing a peristaltic compression which pushes the fluid inside the deformable tube 12 in the flowing direction of said squeezing 54.

Such squeezing expands even to the hollow supporting element 34 and to the longitudinal recess 33. As the supporting element 34 is hollow, it is wholly filled up with said substantially uncompressible fluid which then occupies the whole available inner space, the squeezing 54 of the deformable tube 12 in turn determines a deformation of the supporting element 34 which causes a lateral constriction of the section of deformable tube 12 at the not compressed tube portions and the portions of supporting element 34, designated with 55, caused by the pressure inside the supporting element 34.

In this way, once the squeezing has ceased, the section of the deformable tube 12 immediately returns to its normal, i.e. not stressed, shape.

The localized squeezing 54 then is caused by the interference between the deformable tube and an interfering portion of helical rib 53, which moves by rolling thereon. In the pumping device 36 according to the invention, it is made that at least such interfering portion is revolving around the respective helical axis, while maintaining its own position on the surface of the rotating element 38. In this way, either the interference itself causes a rotation or said at least an interfering portion is made to rotate in another way, such rolling with respect to the rotating element 38 is so as to minimize the friction thereof on the surface of the deformable tube 12 at the squeezing 54, thus decreasing the sliding friction of the rib 53.

In case said at least an interfering portion of rib 53 is made to rotate, it is made to rotate with a rotation direction substantially opposite to the rotation direction of the rotating element 38.

In the peristaltic pumping device 36 according to the herein described embodiment example, said one or more helical ribs 53 consist of one single flexible linear element, structurally independent from the rotating element 38, which wrapped around its surface in helical way with at least two coils, and the flexible linear element, which can be an empty or full tube, a braided rope or a chain, is kept in a prefixed position on the surface of the rotating element 38.

To this purpose, the flexible linear element is kept inside the above-mentioned helical recess 56.

Advantageously, both the linear element and the surface of the rotating element, at least at the helical recess 56, are made of low friction material, and the flexible linear element has a rounded cross section.

In the peristaltic pumping device 36 according to the herein described embodiment example, the whole flexible linear element is driven into rotation around its helical axis, so as to roll on the surface of the deformable tube and with respect to the surface of the rotating element in a direction opposite to the rotation direction of the latter.

To this purpose, the actuator 37 of the pumping device 36, at the ends of the rotating element 38 and of the helical linear element implementing said rib 53, comprises respective actuation mechanisms, designated as a whole with 57.

The two actuation mechanisms 57 are substantially specular and their following description coincides perfectly.

Each actuation mechanism 57 is activated by the rotation of the driven shaft 39 which, at the ends of the rotating element 38, is inserted inside a first pinion 58 fixed on said proximal shaft support 40 and in toothed engagement with a second pinion 59 satellite on the axis thereof a screw shaft 60, integral thereto, is mounted.

The screw shaft 60 is decentralized with respect to the longitudinal axis of the rotating element 38, and the rotation axis thereof is parallel thereto. The screw shaft 60 and the second pinion 59 are revolvingly connected to the respective end wall 61 of the rotating element 38, driving them in rotation therewith.

On the screw shaft 60 a third pinion 62 is arranged in toothed engagement, connected to an actuation fork 64, which is then made to rotate at the end of the rotating element 38, of the surface of the rotating element 38 and of the terminal end of said longitudinal recess 56.

The axis joining the third pinion 62 and the actuation fork 64 is supported revolvingly through a cross septum 63 which is integral to the rotating element 38. In an embodiment version, a V-like insert can be provided, formed by said cross septum 63 and by a triangular portion of the end wall 61, sustaining the second pinion 59, the screw shaft 60, the third pinion 62 and the actuation fork 64. Such V-like insert can be connected to the rotating element 38 which, to this purpose, has a V-like complementary recess. In this way, the mounting of the actuation mechanism 57 in the rotating element is eased.

To the actuation fork 64 two opposite ends of the four ends of an actuation cross-shaped element 65 are revolvingly connected, whereas the other two ends are revolvingly connected to the arms of a yoke 66 which defines a revolving connection, which in turn is connected to the end of the flexible linear element forming said helical rib 53.

Figures 22, 23:
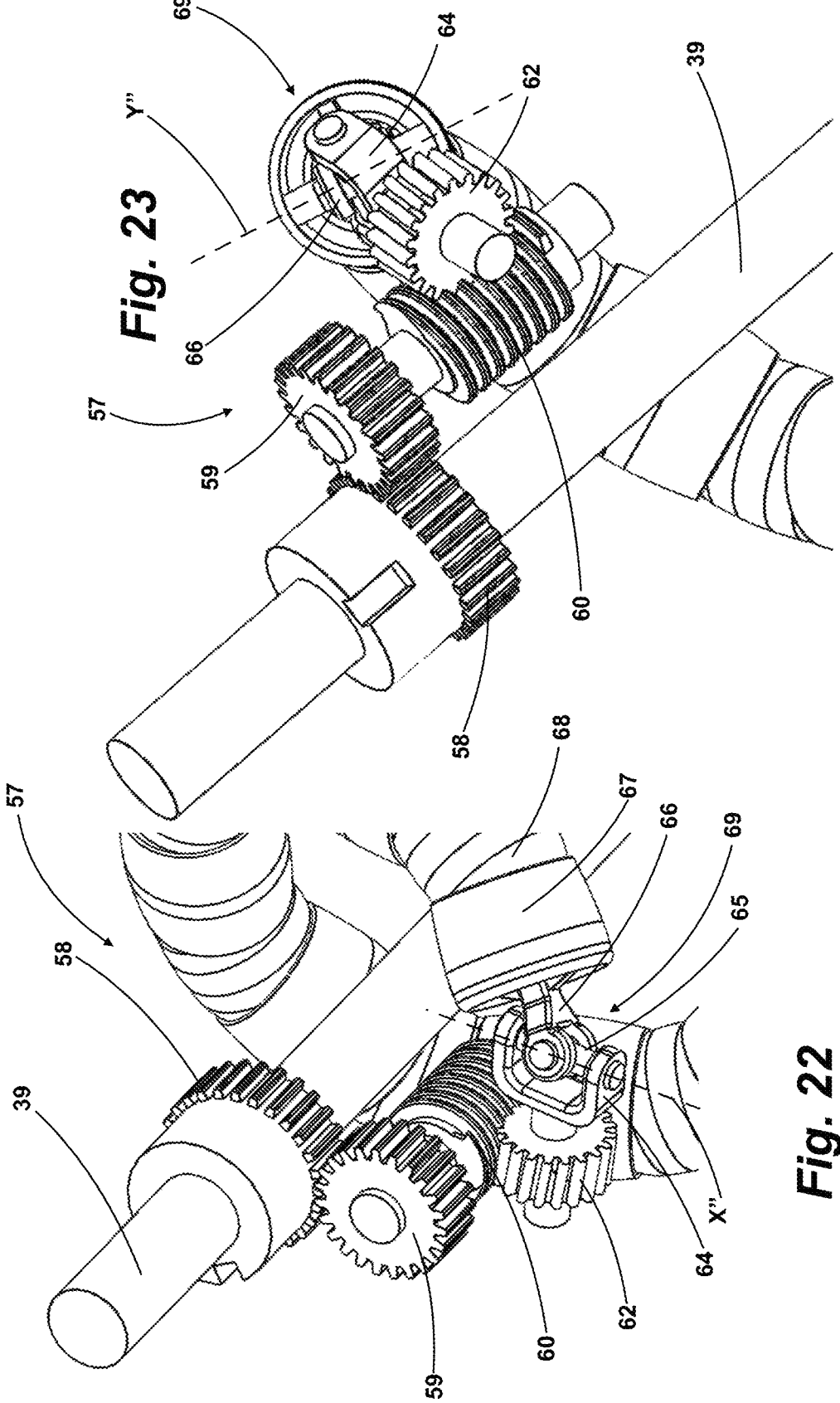
FIGS. 22 and 23 show respective axonometric views of a detail of the portion of the pumping device incorporated in the medical apparatus of FIG. 14, shown isolated, and from two different angulations.
Figures 24, 25, 25A, 26:
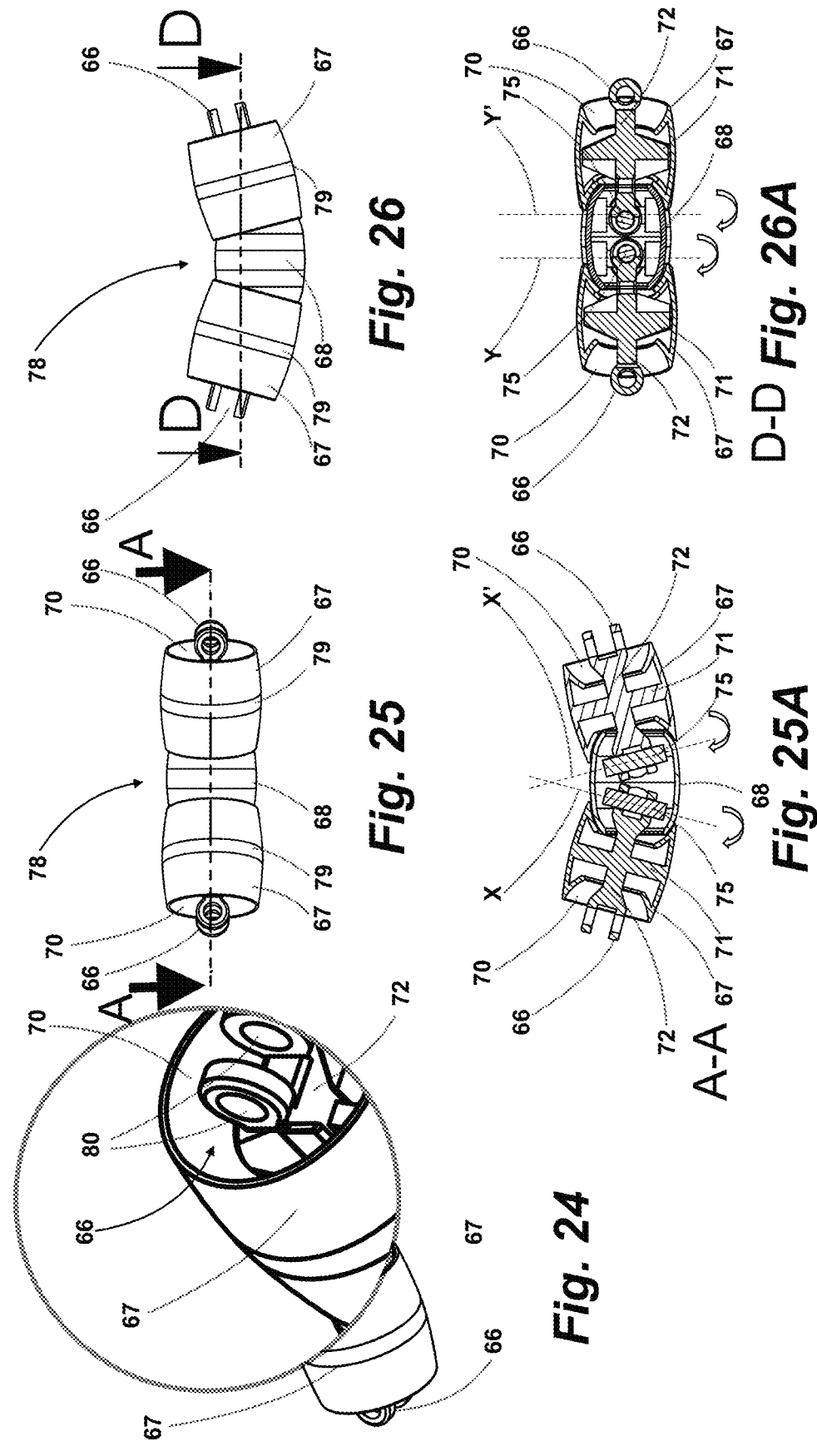
FIG. 24 shows an axonometric view of a chain section belonging to the pumping device incorporated in the medical apparatus of FIG. 1, shown isolated.
FIG. 25 shows a plan view of the chain section of FIG. 24.
FIG. 25A shows a view in longitudinal section of the chain section of FIG. 24, taken along the plane A-A of FIG. 25.
FIG. 26 shows a side view of the chain section of FIG. 24.
Figures 27, 27A, 27B:
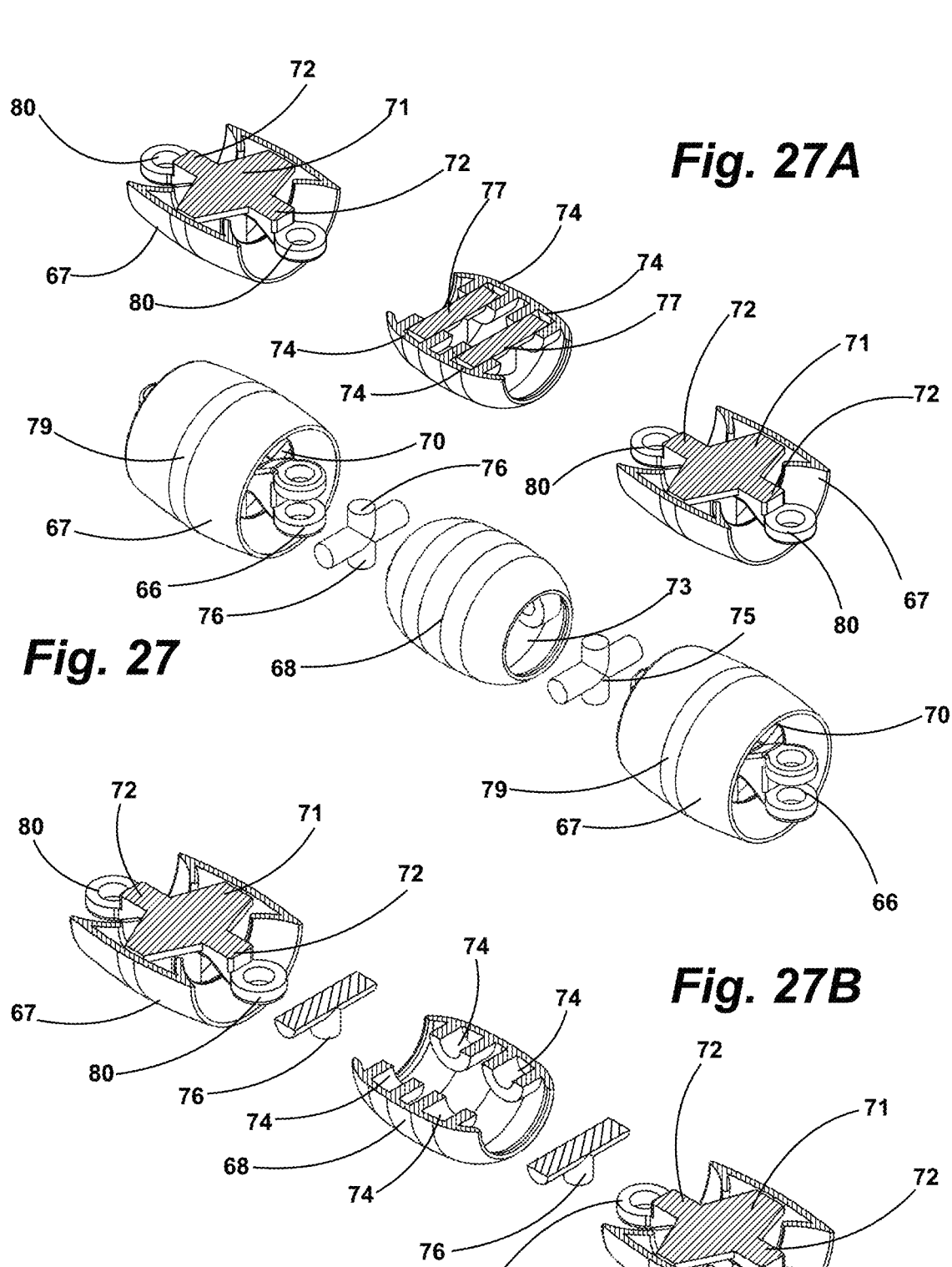
FIG. 27 shows an exploded axonometric view of the chain section of FIG. 24.
FIG. 27A shows a partially exploded axonometric and longitudinal section view of the chain section of FIGS. 24.
FIG. 27B shows another exploded and longitudinal section view of the chain section of FIG. 24.

The actuation fork rotation axes defined by the actuation fork 64 and by the yoke 66, and designated with X" and Y", respectively (FIGS. 22 and 23), are perpendicular therebetween, by implementing together with the actuation cross element 65 an actuation universal, or cardan, joint 69 (FIGS. 22 and 23) which is required so that the orientation of the rotation axis of the third pinion 32 and of the end of the flexible linear element forming said helical rib 53 with respect to the rotation axis of the third pinion 32 varies continuously.

It will be noted that in this way the rotation of the rotating element 38 causes the rotation of the flexible linear element, and then of the interfering portions of helical rib 53, with respect to the rotating element 38 itself and with respect to the section of deformable tube 12.

Moreover, in this way, the rotation of the linear element wound in helical way is proportional to the rotation of the rotating element 38.

Additionally, the transmission ratios between the first pinion 58 and the second pinion 59, and between the screw shaft 60 and the third pinion 62, are so that the resulting transmission ratio of the actuation mechanism between said driven shaft 39 and said rotating element 38 allows to synchronize the forward speed of the compression point and the rotation one of the rotating element 38 by minimizing the sliding friction between the helical rib 53 and the section of deformable tube 12 acting as deformable tube for the peristaltic compression in the pumping device 36.

Advantageously, in the present embodiment example, the linear element is a chain formed by a sequence of chain elements 67 connected therebetween by a junction element 68 interposed between each one thereof, implementing a joint transmitting the motion from a chain element 67 to the other one, by allowing tilting between their rotation axes which, by rotating the chain elements 67 while keeping their position on the surface of the rotating element, or with the respective rotation axes continuously tangent to the helical axis crossing them, varies direction continuously.

Said chain elements 67 and said junctions 68 constitute a sequence of revolving elements which implement together the respective helical rib 53, as they are aligned therebetween along a respective helical axis.

In this embodiment example, each chain element 67 transmits the motion to the adjacent junction element 68 and then to the adjacent chain elements 67, starting from the end chain elements 67 which are driven into rotation by the respective actuation mechanisms 57.

It is to be noted that the possible minimum rotation irregularities due to the mechanical yokes in the connections between chain elements 67 and actuation mechanisms 57, and between the same chain elements 67, are recovered at each rotation by 360°.

It can be understood that, in alternative embodiments, the above-mentioned revolving elements can be independent, mounted on respective supports with respect thereto they are free to rotate due to the effect of their interference with the deformable tube 12.

Alternatively, they can be still independent, but their rotation can be controlled by a suitable mechanism, in case synchronized with the rotation of the rotating element 38 and/or inside thereof.

Going back to the present embodiment example, the above-mentioned end of the flexible linear element forming said helical rib 53 is defined by a chain element 67, which is driven into rotation by the above-mentioned actuation universal joint 69. It transmits the motion to the subsequent junction element 68 which transmits it to the following chain element 67 and so on, and this for both chain ends.

The chain element 67 has a substantially barrel-like shape, with a circumferential convexity 79 at its transverse centreline plane; it has two respective first open ends 70. Internally, at its transverse centreline plane it comprises a reinforcement septum 71, arranged where the interaction of the rib 53 with the deformable tube exerts the higher pressure. Moreover, on its longitudinal axis it comprises a plug 72 crossing the chain element 67 from side to side.

At each one of the first open ends, the plug 72 forms a respective yoke 66, slightly projecting outside with two slots 80 which define, on the opposite ends of the chain element 67, respective first transverse rotation axes X, X', parallel therebetween. Such yoke 66 corresponds to the one described with reference to the end of the flexible linear element forming said helical rib 53.

The junction element 68 has a substantially cylindrical shape, slightly rounded in the centre, and it too has respective second open ends 73 which make accessible the inside of the junction element 68. Its end diameter is so as to go back inside the open ends 70 of the chain element 67, with a sufficient yoke so as to allow their mutual tilting allowing their longitudinal axes to stay substantially tangent to the helical axis of the helical rib 53.

The junction element 68 comprises inside thereof two respective pairs of seats of pin 74 arranged faced so as to define a respective second transverse rotation axis Y, Y', parallel therebetween. Each pair of seats of pin 74 is positioned between the centreline and the respective second open end 73.

The chain then comprises, between each one of the chain elements 67 and the 20) junction elements 68, a chain cross element 75, shaped like a cross, which defines two pairs of opposite first and second cross pins 76, 77, the first and second pins 76, 77 being perpendicular and coplanar therebetween.

The first cross pins 76 are arranged in revolving engagement in the slots 80 of each yoke 66, whereas the second cross pins 77 are arranged in revolving engagement in said seats of pin 74.

In this way, between the chain element 67 and the junction element 68 a chain universal joint is implemented and, as a whole, the junction element 68 forms a double-cardan joint 78 joining the chain elements 67.

In this way, the motion between the two rotation axes of two subsequent chain elements 67 is transmitted by a joint which implements a coupling substantially of cardan type.

The chain elements 67 and the junction elements 68 can consists of respective half-elements defined by a longitudinal separation plane, which can be coupled therebetween to the cross element 75 by joining by welding or gluing, in the process of their assembly.

However, these three separate portions forming the chain, i.e. the whole chain, can be obtained together by means of an additive moulding process (three-dimensional moulding), without requiring an assembly step.

The apparatus 1 according to the present embodiment example comprises a selective clamping device, designated as a whole with 81, to monitor the fluid flow through the pumping device 36.

It is arranged in suspension on the second interior wall 9 of the upper portion 3, at the distal side 17 of the base portion, in order to clamp selectively the connecting lines 16, relating to the bags for loading and discharging the dialysis solution.

The clamping device 81 of the present embodiment example comprises a second motor 82, in particular an electric step motor, powered and controlled through the control unit 26 which even receives the signal of possible position sensors of the movable portions which will be described hereinafter.

The second motor 82 is received in the central area 95 of the upper compartment 11 of the upper portion 3, in a substantially opposite position with respect to that of the first motor 46. Even the longitudinal axis of the second motor 82, for space reasons, is arranged parallel to the longitudinal axis of the rotating element 38.

The second motor 82 comprises a respective second driving shaft 83 crossing the distal dividing septum 94 which is adjacent thereto (FIG. 8) and sustains it. Apart from the distal dividing septum 94 it comprises a control screw section 84, whereon a fourth pinion 85, which is in toothed engagement therewith, is actuated.

The fourth pinion 85 drives in rotation a control shaft 86 whereon four cams 87 are arranged in sequence, arranged side by side and equal therebetween and suitably staggered therebetween according to a fixed angle, for monitoring the clamping of four connecting lines 16. The cams 87 and the above-described actuations are included in the distal area 96 of the upper compartment 11 of the base portion, behind said second interior wall 9.

It is to be meant that, upon varying the number of connecting lines, even the number of cams 87 could vary and they will be always staggered by the same angular distance.

Each cam 87 has a cylindrical profile 88 which interrupts due to a cam recess 89 having, in the centre thereof, a respective cam tooth 90.

The cams 87 are operatively adhered to a respective cam follower 91 even through a not represented elastic system. The clamping device 81 then comprises four cam followers 91, each one corresponding to a respective cam 87.

When the upper portion 3 is in a closed configuration, the control shaft 86 extends transversally at the branching 15, and the cams 87 are each one in a position which corresponds to a respective connecting catheter 16.

Each cam 87 has a cylindrical profile 88 which interrupts due to a first cam recess 89 having, in the centre thereof, a respective cam tooth 90.

The cams 87 are operatively adhered to a respective cam follower 91. The clamping device 81 then comprises four cam followers 91, each one corresponding to a respective cam 87.

The cam followers 91 are articulated to an axial fulcrum 92, arranged transversally parallel to the control shaft 86.

With its rotation, the control shaft 86 rotates all cams 87 together, so that only one thereof at a time is in a position so as to allow the fluid passage in the corresponding connection line, whereas the other lines are clamped and then wholly obstructed.

The cams 87 further include a second cam recess 110 positioned according to an angle which implements an overall alignment thereof, this configuration allows to obtain a neutral angular position of the clamping system in which no line 16 results to be obstructed.

Figures 10, 11, 12, 13:
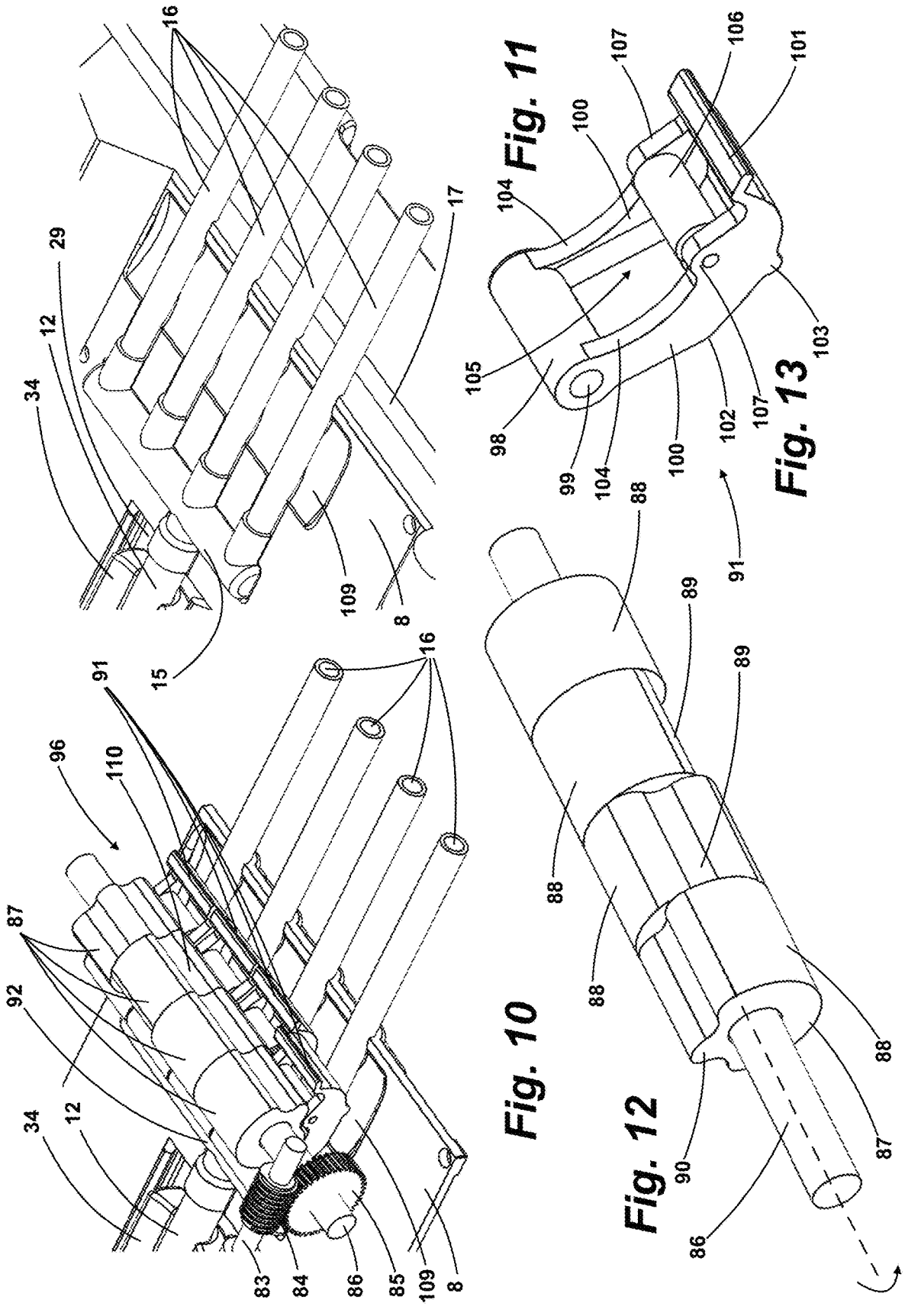
FIG. 10 shows an enlarged axonometric view of a detail of the medical apparatus and of the section of kit for peritoneal dialysis of FIG. 1, in open configuration.
FIG. 11 shows an axonometric view of the first detail of FIG. 10, without some portions thereof.
FIG. 12 shows an axonometric view of one of the portions of the first detail of FIG. 10, not visible in FIG. 11.
FIG. 13 shows an axonometric view of another one of the portions of the first detail of FIG. 10, not visible in FIG. 11.
Figures 14, 15:
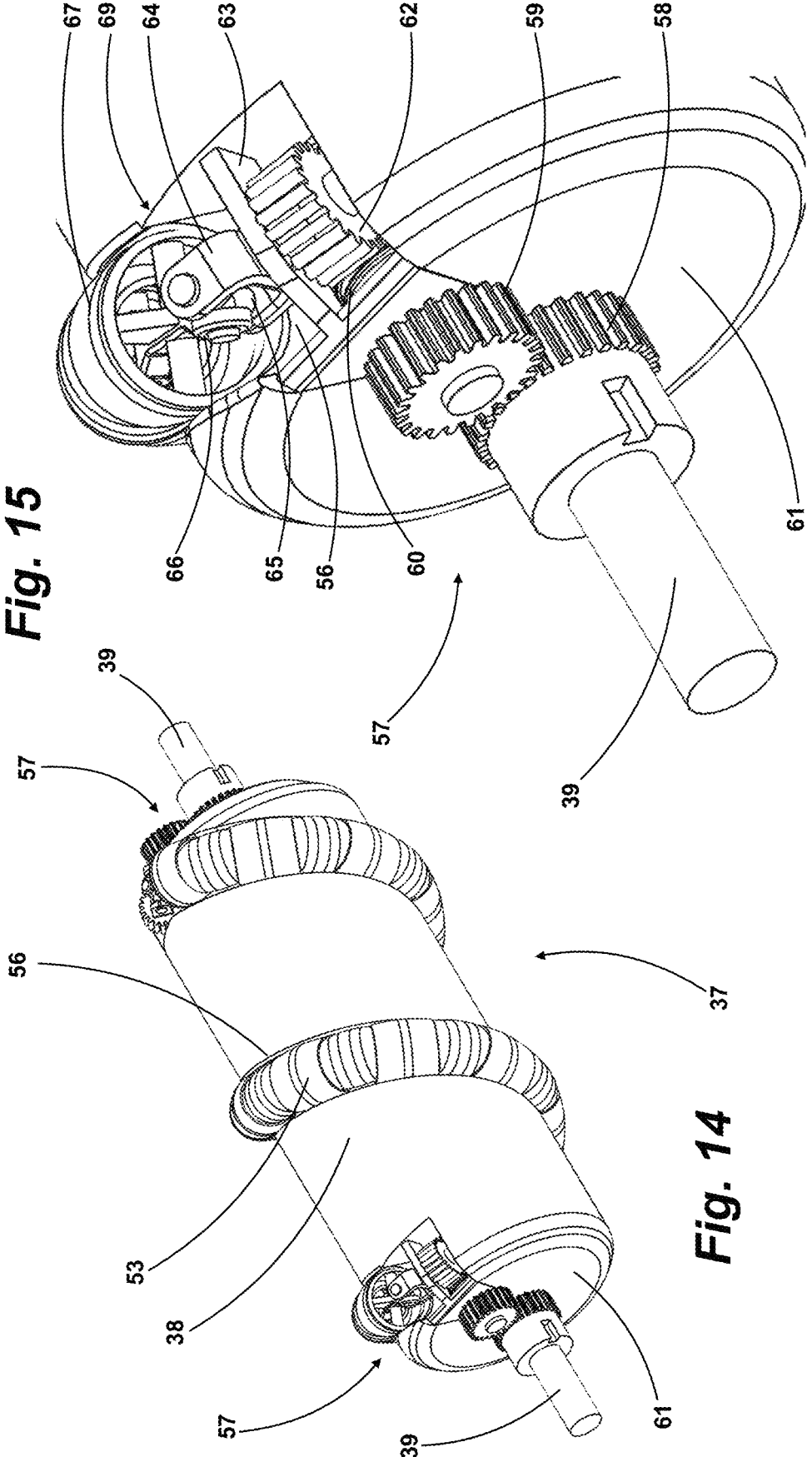
FIG. 14 shows an axonometric view of a portion of the pumping device incorporated in the medical apparatus of FIG. 1.
FIG. 15 shows an enlarged axonometric view of the portion of the pumping device of FIG. 14.

The cam follower 91 (FIG. 13) comprises a knuckle 98 with a through-hole 99 engaged by the axial fulcrum 92. From the knuckle 98 a pair of arms 100 extend as far as ends connected by a transversal bar 101. The arms 100 are arched and have a convex edge 102, therefrom a clamping tooth 103 projects, and a concave edge 104 delimitating an indentation 105 comprised between the knuckle and a roller 106 extending from an arm 100 to the other one, revolvingly supported above the respective concave edge 104 by a supporting projection 107.

Moreover, the second interior wall 9 comprises a second window 108 which exposes said cam followers, with the clamping tooth 103 projecting therefrom: the cam followers 91 then are arranged to be lowered and raised from the rotation of the respective cams 87 acting as clamping pressure elements, by squeezing a point of the respective connecting catheter 16 on a squeezing area 109 of the first interior wall 8.

In the rotation of the cams 87, when the cylindrical profile 88 presses on the roller 106, the clamping tooth 103 is pushed towards the respective connecting catheter 16. On the contrary, when the cam tooth 90 enters the indentation 10, it engages below the roller 106, in this way by raising the cam tooth 103 and the whole cam follower 91, determining the selective closure or opening of said lines 16.

As far as the operation of the medical apparatus 1 is concerned, it is required to insert the section of kit for peritoneal dialysis 31 in its seat 30, arranging its portions in the base recess 29 and in the linear seat 32. The asymmetric geometry of said kit obliges 30) the correct insertion thereof.

When this procedure is performed with the apparatus 1 in wholly open configuration, it is possible to re-close the upper portion 3 on the base portion, and lock the handle 5 in its closing position.

It is possible to provide for that, if the insertion of the section of kit for peritoneal dialysis 31 in its seat 30 has not been successfully, the complete closing of the apparatus 1 and the positioning of the handle 5 with the teeth 6 in their recesses 7 is not possible, with a poka-yoke mechanism, or with other similar devices.

The complete closing of the apparatus 1 enables the operation thereof.

After having switched on the apparatus 1, it is possible to start a programme of peritoneal dialysis customized on the patient, the data thereof have been already inserted in the memory of the control unit.

In case, the apparatus 1 can be provided with a wireless connectivity to the network, with the possibility of accessing to a dedicated server where, after authentication, it is possible to access remotely to such customized programme, prepared by qualified medical personnel.

The user, either the patient himself/herself or an assistant thereof, has to take care of performing correctly the required connections of the section of kit for peritoneal dialysis 31 to the loading and discharge bags and to the abdominal catheter.

The data related to the bags, such as the capacity, can be inserted in the memory of the control unit as process operating data. In case, it is possible to provide the apparatus with a reader capable of obtaining this information from a removable mass memory, a QR code or a RFID tag.

It is also possible to enable the apparatus 1 to a portable electronic device, such as a smartphone or a tablet, so that these functions could be carried out through such instrument, with the intermediation of a suitable application installed on the device.

Once performed these preliminary procedures, it is possible to start the real operation of the apparatus, which provides for making to flow, with the correct timing, a first amount of dialysis solution from a first loading bag; if such amount is not sufficient, the apparatus provides for selecting the outflow from a second loading bag until the insertion of the solution has reached the wished amount. During the outflow, all physiological parameters of the dialysis solution, such as temperature and pressure, can be monitored and, if they do not fall within precise parameters, the insertion is interrupted and an alarm is actuated.

Once the period of real dialysis is concluded, the apparatus 1 provides for extracting the exhausted solution from the patient's abdomen, by sending it to a respective loading bag, and should it be not sufficient, the apparatus can enable the discharge to an additional bag.

The execution of a more complex programme can be provided, with a first step of washing the abdominal cavity with a suitable washing solution, which is then extracted and discharged in a destination bag, and a second step of real dialysis, as described previously.

The solution volume to be inserted, the length of the waiting interval and the exhausted solution volume to be extracted could be determined during setting and customizing the device for a predetermined patient.

Once the extraction is ended, the process ends up by enabling the re-opening of the apparatus 1, therefrom it will be possible to extract the section of kit for peritoneal dialysis 31 which could be disposed of as special waste.

To the above-described linear peristaltic pumping device and to the medical apparatus incorporating it, a person skilled in the art, with the purpose of satisfying additional and contingent needs, could introduce several additional modifications and variants, however all within the protective scope of the present invention, as defined by the enclosed claims.

The invention claimed is:

1. A peristaltic pumping device of linear type, comprising:
   a section of deformable tube crossed by a fluid whereon at least one peristaltic compression is implemented; and
   an actuator, comprising a rotating element provided with one or more helical ribs arranged to project from the surface thereof so as to interfere, along the rotation of the rotating element, with said deformable tube thereby causing thereon at least a localized, movable and continuous squeezing, moving along a predetermined direction, implementing peristaltic compression, said one or more helical ribs being spirally wound along a respective helical axis with respect thereto the position thereof is tied onto the surface of the rotating element,
   wherein at least one portion of said one or more helical ribs is rotatable with respect to said helical axis, and rotates therearound at least when said at least one portion of said one or more helical ribs interferes with said deformable tube, thereby minimizing the friction thereof on a tubular surface of the deformable tube.

2. The peristaltic pumping device according to claim 1, wherein said section of deformable tube is arranged in a linear layout inside a linear seat having a bottom thereupon a lower surface of the section of deformable tube is rested, whereas an upper surface of the section of deformable tube is facing towards said actuator of the pumping device.

3. The peristaltic pumping device according to claim 2, wherein said linear seat comprises a longitudinal recess wherein said section of deformable tube is inserted, and a hollow supporting element with deformable walls, in which said longitudinal recess is formed, wherein the hollow supporting element is wholly sealingly filled up with a substantially incompressible fluid, which then occupies the whole available inner space, a squeezing of the deformable tube in turn determining a deformation of the supporting element at the squeezing which causes a shifting of the incompressible fluid inside the supporting element which, at the not compressed portions of deformable tube, causes a lateral constriction of the section of deformable tube caused by the pressure inside the supporting element.

4. The peristaltic pumping device according to claim 1, wherein the at least one portion of said one or more helical ribs is made to rotate with a rotation direction substantially opposite to the rotation direction of the rotating element.

5. The peristaltic pumping device according to claim 1, wherein said one or more helical ribs consist of one single flexible linear element, structurally independent from the rotating element, spirally wound in a helical pattern around it and kept in a fixed position on its surface.

6. The peristaltic pumping device according to claim 5, wherein said flexible linear element is driven into rotation around its helical axis, so as to roll on the surface of the deformable tube.

7. The peristaltic pumping device according to claim 6, wherein the rotation of the flexible linear element is synchronized with the rotation of the rotating element, the actuator comprising at least a mechanism for activating the rotation of the flexible linear element.

8. The peristaltic pumping device according to claim 7, wherein the above-mentioned synchronization is so that to the rotation of the rotating element a proportional rotation of the linear element corresponds, wound in a helical way around its helical axis, according to a predetermined ratio which determines, on the deformable tube, a pure rolling.

9. The peristaltic pumping device according to claim 7, wherein said activation mechanism is activated by the rotation of a driven shaft of the rotating element, comprising a respective first pinion rotating in toothed engagement with a second pinion transmitting the rotation to an end of the flexible linear element, and wherein on said second pinion a screw shaft is mounted, integral thereto, which is revolvingly connected to the rotating element driving them in rotation, a third pinion being arranged in toothed engagement on the screw shaft, connected to an actuation fork thereto two opposite ends of the four ends of an actuation cross-shaped element are revolvingly connected, whereas the other two ends are revolvingly connected to the arms of a yoke which defines a revolving connection, which in turn is connected to the end of the flexible linear element, the actuation fork rotation axes defined by the actuation fork and by the yoke being perpendicular therebetween, by implementing a universal actuation joint.

10. The peristaltic pumping device according to claim 5, wherein on the rotating element a helical recess is obtained acting as seat of the flexible linear element which in turn comprises at least a winding on the rotating element, so as to compress the deformable tube in at least two spaced points.

11. The peristaltic pumping device according to claim 5 wherein the flexible linear element is a chain formed by a sequence of chain elements connected therebetween by a joint which implements a coupling substantially of cardan type.

12. The peristaltic pumping device according to claim 11, wherein the chain element has a substantially barrel-like shape, with a circumferential convexity, and it comprises inside, at its transverse centerline plane, a reinforcement septum, arranged where the interaction of the rib with the deformable tube exerts a higher pressure than other portions.

13. The peristaltic pumping device according to claim 11, wherein the chain element has two respective open ends and a plug crossing the chain element from side to side and comprising, at each one of the open ends, a respective yoke which defines, on the opposite ends of the chain element, respective first transverse rotation axes, being provided:
   a junction element, with substantially cylindrical shape, interposed in said chain between two adjacent chain elements, which has respective open ends and, inside thereof, two respective pairs of seats of pin arranged faced so as to define a respective second transverse rotation axis, parallel therebetween; and
   an actuator cross-shaped element, which defines two pairs of opposite first and second pins perpendicular and coplanar therebetween, inserted in each yoke and in said seats of pin, respectively,
   by implementing a double cardan joint.

14. The peristaltic pumping device according to claim 11, wherein portions composing said chain have a shape so that the chain can be obtained by means of an additive printing process in which such portions are formed.

15. The peristaltic pumping device according to claim 1, wherein said one or more helical ribs consists of a sequence of independent revolving elements, aligned therebetween along a respective helical axis.

16. A medical apparatus for peritoneal dialysis, comprising a pumping device according to claim 1, and at least one kit for peritoneal dialysis which provides a section of deformable tube for the pumping device, comprising a branching with a plurality of connecting lines.

17. The medical apparatus according to claim 16, further comprising a selective clamping device, acting on said plurality of connecting lines of the at least one kit for peritoneal dialysis.

18. The medical apparatus according to claim 16, further comprising a plurality of cams, corresponding to said plurality of connecting lines, staggered therebetween and controlled as a whole in rotation by a control shaft, so as to selectively actuate respective cam followers provided with a respective clamping tooth acting on a corresponding connecting catheter.

19. The medical apparatus according to claim 16, further comprising an operating seat for disposing said at least one kit for peritoneal dialysis inside complementary thereto, thus preventing the use of inappropriate kits, or an improper use of the pumping device.

20. The medical apparatus according to claim 19, wherein the at least one kit for peritoneal dialysis comprising at least a seat of sensors in a predetermined position.

\* \* \* \* \*